US008372657B2

(12) United States Patent
Reboud et al.

(10) Patent No.: US 8,372,657 B2
(45) Date of Patent: Feb. 12, 2013

(54) MICROFLUIDIC SYSTEM FOR DETECTING A BIOLOGICAL ENTITY IN A SAMPLE

(75) Inventors: Julien Reboud, Glasgow (GB); Linus Tzu-Hsiang Kao, Singapore (SG); Andre Yao-Kuang Chung, Singapore (SG); Shin Yun Ng, Singapore (SG); Yu Chen, Singapore (SG); Yan Ping Wang, Singapore (SG); Janice Hao Yuan Liaw, Singapore (SG); Kum Cheong Tang, Singapore (SG)

(73) Assignee: Agency For Science, Technology, and Research, Singapore (SG)

( * ) Notice: Subject to any disclaimer, the term of this patent is extended or adjusted under 35 U.S.C. 154(b) by 0 days.

(21) Appl. No.: 12/908,561

(22) Filed: Oct. 20, 2010

(65) Prior Publication Data

US 2011/0129931 A1 Jun. 2, 2011

(30) Foreign Application Priority Data

Oct. 20, 2009 (SG) .................................. 200906999-8

(51) Int. Cl.
*G01N 1/18* (2006.01)
*G01N 33/48* (2006.01)
*C12M 1/34* (2006.01)

(52) U.S. Cl. .......... 436/180; 436/63; 436/149; 436/150; 436/174; 436/177; 436/178; 435/29; 435/34; 435/372; 435/287.1; 435/287.3; 435/288.4; 435/288.5; 422/82.01; 422/502; 422/513; 422/527; 422/534; 422/535; 422/68.1

(58) Field of Classification Search .................. 436/501, 436/518, 524, 531, 532, 63, 71, 149, 150, 436/174, 175, 177, 178, 180; 435/2, 4, 5, 435/6.1, 7.1, 29, 30, 34, 325, 326, 366, 372, 435/372.2, 372.3, 287.1, 287.2, 287.3, 288.3, 435/288.4, 288.5; 422/82.01, 82.02, 502, 422/503, 504, 507, 513, 527, 534, 535, 68.1; 506/39

See application file for complete search history.

(56) References Cited

U.S. PATENT DOCUMENTS

| 5,776,709 A | 7/1998 | Jackson et al. |
| 7,416,892 B2 | 8/2008 | Battrell et al. |
| 2002/0076825 A1* | 6/2002 | Cheng et al. .................. 436/174 |
| 2005/0067279 A1 | 3/2005 | Chen et al. |

(Continued)

FOREIGN PATENT DOCUMENTS

| EP | 1 484 390 A1 | 12/2004 |
| WO | WO 2010/050898 A1 | 5/2010 |

OTHER PUBLICATIONS

Asahara, T. et al., *Isolation of Putative Progenitor Endothelial Cells for Angiogenesis*, Science, vol. 251, (1997), pp. 964-967.

(Continued)

*Primary Examiner* — Maureen Wallenhorst
(74) *Attorney, Agent, or Firm* — Alston & Bird LLP

(57) ABSTRACT

According to various embodiments, a microfluidic system for detecting a biological entity in a sample volume is provided. The microfluidic system may include: a chamber configured to receive the sample volume, wherein the chamber includes a detection region for detecting the biological entity; a first port in fluid communication with the chamber; and a second port including a filter in fluid communication with the chamber; and wherein a fluid provided to the first port or the second port flows between the first port and the second port through the chamber.

28 Claims, 28 Drawing Sheets

U.S. PATENT DOCUMENTS

| | | | |
|---|---|---|---|
| 2006/0205085 A1* | 9/2006 | Handique et al. | 436/177 |
| 2006/0263265 A1 | 11/2006 | Kang et al. | |
| 2007/0003527 A1* | 1/2007 | Shieh | 424/93.7 |
| 2008/0013092 A1 | 1/2008 | Maltezos et al. | |
| 2008/0047832 A1 | 2/2008 | Cheng et al. | |
| 2009/0152215 A1 | 6/2009 | Ahn et al. | |

OTHER PUBLICATIONS

Chen, Y. et al., *Compact Microelectrode Array System: Tool for in Situ Monitoring of Drug Effects on Neurotransmitter Release from Neural Cells*, Analytical Chemistry, vol. 80, No. 4, (2008), pp. 1133-1140.

Chen, X. et al., *Microfluidic Chip for Blood Cell Separation and Collection.Based on Crossflow Filtration*, Sensors and Actuators B 130 (2008), pp. 216-221.

Chung, T. D. et al., *Recent Advances in Miniaturized Microfluidic Flow Cytometry for Clinical Use*, Electrophoresis 28, (2007), pp. 4511-4520.

Estes, M. D. et al., *On Chip Cell Separator Using Magnetic Bead-Based Enrichment and Depletion of Various Surface Markers*, Biomed Microdevices 11, (2009), pp. 509-515.

Hill, J. M. et al., *Circulating Endothelial Progenitor Cells, Vascular Function, and Cardiovascular Risk*, The England Journal of Medicine, (2003), pp. 593-600.

Jokerst, J. V. et al., *Integration of Semiconductor Quantum Dots into Nano-Bio-Chip Systems for Enumeration of CD4+T Cell Counts at the Point-of-Need*, The Royal Society of Chemical, Lab Chip, 8, (2008), pp. 2079-2090.

Khan, S. S. et al., *Detection of Circulating Endothelial Cells and Endothelial Progenitor Cells by Flow Cytometry*, Cytometry Part B (clinical Cytometry), 64B, (2005), pp. 1-8.

Liu, R. H. et al., *Self-Contained, Fully Integrated Biochip for Sample Preparation, Polymerase Chain Reaction Amplification, and DNA Microarray Detection*, Analytical Chemistry, vol. 76, No. 7, (2004), pp. 1824-1831.

Massa, M. et al., *Increased Circulating Hematopoietic and Endothelial.Progenitor Cells in the Early Phase of Acute Myocardial Infarction*, The American Society of Hematology, Blood, vol. 105, No. 1, (2005), pp. 199-206.

Mocellin, S. et al., *Circulating Tumor Cells: The 'Leukemic Phase' of Solid Cancers*, TRENDS in Molecular medicine, vol. 12, No. 3, (2006), pp. 130-139.

Nagrath, S. et al., *Isolation of Rare Circulating Tumour Cells in Cancer Patients by Microchip Technology*, Nature Publishing Group, vol. 450, (2007), pp. 1235-1239.

Ng, S. Y. et al., *Label-Free Impedance Detection of Low Levels of Circulating Endothelial Progenitor Cells for Point-of-Care Diagnosis*, Biosensors and Bioelectronics 25, (2010), pp. 1095-1101.

Roeser, T. et al., *Lab-on-Chip for the Isolation and Characterization of Circulating Tumor Cells*, Proceedings of the 29th Annual International Conference of the IEEE EMBS, Lyon, France (2007), pp. 6446-6448.

Rosenzweig, A., *Circulating Endothelial Progenitors—Cells as Biomarkers*, The New England Journal of Medicine, (2005), pp. 1055-1057.

Sethu, P. et al., *Continuous Flow Microfluidic Device for Rapid Erythrocyte Lysis*, Analytical Chemistry, vol. 76, No. 21, (2004), pp. 6247-6253.

Shaffer, R. G. et al., *Flow Cytometric Measurement of Circulating Endothelial Cells: The Effect of Age and Peripheral Arterial Disease on Baseline Levels of Mature and Progenitor Populations*, International Society for Analytical Cytology, Cytometry Part B (Clinical Cytometry), 70B, (2006), pp. 56-62.

Szmitko, P. E. et al., *Endothelial Progenitor Cells: New Hope for a Broken Heart*, Journal of the American Heart Association, (2003), pp. 3093-3100.

Vona, G. et al., *Isolation by Size of Epithelial Tumor Cells; A New Method for the Immunomorphological and Molecular Characterization of Circulating Tumor Cells*, American Journal of Pathology, vol. 156, No. 1, (2000), pp. 57-63.

Wang, Y. et al., *On-Chip Counting the Number and the Percentage of CD4+T Lymphocytes*, The Royal Society of Chemistry, Lab Chip, 8, (2008), pp. 309-315.

Zheng, S. et al., *Membrane Microfilter Device for Selective Capture, Electrolysis and Genomic Analysis of Human Circulating Tumor Cells*, Journal of Chromatography A, 1162 (2007), pp. 154-161.

*Standardized Enumeration of Human Endothelial Progenitor Cells (EPCs) Based on a Flow Cytometric Assay*, MACS Miltenyi Biotec (undated).

Welcome to ACEABIO.com—Technology—Overview. . . [online] [retrieved Dec. 28, 2010]. Retrieved from the Internet: <URL: http://www.aceabio.com/Technology/index.htm>. 2 pages.

* cited by examiner

MICROFLUIDIC SYSTEM FOR DETECTING A BIOLOGICAL ENTITY IN A SAMPLE

CROSS-REFERENCE TO RELATE APPLICATIONS

This application claims the benefit of priority of Singapore application No. 200906999-8, filed 20 Oct. 2009, the content of it being hereby incorporated by reference in its entirety for all purposes.

TECHNICAL FIELD

Various embodiments relate to a microfluidic system for detecting a biological entity in a sample volume and a method of forming the microfluidic system. Various embodiments further relate to a method for detecting a biological entity using the microfluidic system.

BACKGROUND

The number of circulating cells in the blood of patients is a routinely used biomarker in clinical diagnostics. However, the current systems used to detect them are bulky, expensive, time-consuming and require external sample preparation procedures. In addition, microfluidic devices have been utilized, providing compact and cheap solutions that may offer promise to move the testing towards the patient in a bedside setting. Unfortunately, these techniques often require a certain amount of sample preparation, especially when using label-free approaches to achieve a good efficiency.

Recent developments have included using specific sub-populations of cells as biomarkers for various diseases. Sub-types of circulating cells have been used as diagnostic biomarkers for various conditions, for example circulating tumour cells (CTCs) for cancer (Mocellin S. et al., "Circulating tumor cells: the 'leukemic phase' of solid cancers", TRENDS in Molecular Medicine, 2006, 12 (3), 130-139), lymphocytes CD4 for HIV (Jokerst J V. et al., "Integration of semiconductor quantum dots into nano-bio-chip systems for enumeration of CD4+ T cell counts at the point-of-need", Lab Chip, 2008, 8, 2079-2090) and endothelial progenitor cells for cardiovascular conditions (Massa M. et al., "Increased circulating hematopoietic and endothelial progenitor cells (EPCs) in the early phase of acute myocardial infarction", Blood, 2005, 105: 199-206). These biomarkers can be used for early diagnostics, prognosis, therapy monitoring or minimal residual disease controls. Their numbers in blood can vary from extremely low, for example <5 cells per 7.5 ml for CTCs, to relatively abundant, for example 200 cells/µl for CD4 T-lymphocytes, with EPCs around 0.01%-2% of peripheral blood mononuclear cells (PBMCs), while blood contains about 7000-10000 white blood cells and 1000 times more red blood cells. This poses a great challenge for biosensor applications requiring very low detection limits in order to detect the biomarkers in the blood.

The number of circulating cells has been used as a diagnosis marker in conventional procedures, such as the white blood cell counts which are performed routinely in the clinical labs. EPCs have also been used as biomarkers of cardiovascular conditions. Circulating EPCs are stem cells derived from the bone marrow with the ability to differentiate into vascular endothelial cell for blood vessel lining repair and their number in blood may be used as a biomarker (Rosenzweig A., "Circulating Endothelial Progenitors—Cells as Biomarkers", The New England Journal of Medicine, 2005, 353 (10), 1055-1057; J. M. Hill et al., "Circulating Endothelial Progenitor Cells, Vascular Function, and Cardiovascular Risk", The New England Journal of Medicine, 2003, 348, 593-600; P. E. Szmitko et al., "Endothelial progenitor cells: new hope for a broken heart", Circulation, 2003, 107, 3093-100). EPC levels may be used for health monitoring as their levels in blood correlate to the coronary artery diseases or cardiovascular conditions and their risk factors. EPCs are also used for therapy monitoring to monitor the effects of primary and secondary prevention strategies, where specific drugs, such as statins, are known to increase the EPC counts. In addition, EPCs can be transplanted for tissue regeneration.

However, analyzing specific subtypes of circulating cells is not a trivial matter and has not been used as a common practice due to technical limitations and relatively high costs. Effective and selective extraction of rare target cells from whole blood has been very challenging for the micro total analysis systems (µTAS). A 1 µl whole blood sample may contain approximately 4-5 millions of red blood cells (RBCs) and approximately 4-11 thousands of peripheral blood mononuclear cells (PBMCs). Assuming detection of CD34+ cells at the level of 0.1% PBMCs, this will imply as few as 7 cells in 1 µl of whole blood. Conventionally, a sample preparation assay for cell purification is required in order to separate such a low concentration of EPCs from blood. Typical procedures include: (1) incubate sample with RBC lysis buffer, (2) centrifuge the cell suspension and remove the supernatants, (3) label with magnetic beads which are tagged with antigen-specific antibodies and (4) centrifuge again and remove unbound beads in the solution. The overall time for the sample preparation process may be around 1-2 hours and in addition, the process requires a bulky centrifuge machine and skilled personnel. Consequently, these present limitations for the use of conventional sample purification assay for point-of-care applications.

The cell sub-types are usually defined by their expressions of specific surface markers. For example, the detection of CTCs is generally based on the presence of the specific epithelial marker, epithelial cell adhesion molecule (EpCAM), on their surface, while EPCs can be defined by its CD34 or CD133 protein or the endothelial marker protein, VEGFR2/KDR or a combination of these proteins. In order to detect these specific cells, the conventional technique is the flow cytometry analysis (Khan S. S. et al., "Detection of Circulating Endothelial Cells and Endothelial Progenitor Cells by Flow Cytometry", Clinical Cytometry, 2005, 64B, 1-8), such as the fluorescent cell sorter (FACS) which optically reads the fluorescence of cells stained with a specific marker passing through a thin capillary. However, this technique is cumbersome, time-consuming (approximately 4-5 hours for the staining process and analysis), require large sample volumes (>1 ml), demands highly skilled personnel and is generally performed off-site.

With the advent of microfluidics, approaches have emerged which aim to overcome the disadvantages of the FACS (ie. the time and skill involved) and enhance portability. Flow-through systems (Taek Dong Chung, Hee Chan Kim, "Recent advances in miniaturized microfluidic flow cytometry for clinical use", Electrophoresis, 2007, 28, 4511-4520) directly miniaturize the sorting concept and use specific properties of the cells to direct them to counters, for detection by means of either optical or label-free (Roeser T. et al., "Lab-on-chip for the Isolation and Characterization of Circulating Tumor Cells", Proceedings of the 29th Annual International Conference of the IEEE EMBS, 2007, 6446-6448), or both (Wang Y-N et al, "On-chip counting the number and the percentage of CD4+ T lymphocytes", Lab Chip, 2008, 8, 309-315). These systems enable precise counting of the cells passing through, but require preliminary off-chip sample preparation, for example involving fluorescent or magnetic staining, and which may also include separating the PBMCs. Furthermore, flow-through systems may result in cell loss and may not be suitable for large sample processing, which will affect costs and sensitivity/specificity issues. The process of labeling or staining the cells is also time-consuming.

"Flow-stop" systems are also available, which use the specific binding of the cells on the functionalized surfaces of the microdevices to purify the sample directly on the chip from whole blood (Nagrath S. et al. "Isolation of rare circulating tumour cells in cancer patients by microchip technology", Nature, 2007, 450, 1235-1239). However, detection is performed optically after fluorescent staining and requires a complicated optical analysis system to automate, and with a relatively poor efficiency.

The use of additional labels has prevented the conventional devices from achieving point-of-care detection in a portable manner, with a speed that is amenable for diagnosis of acute diseases, for example <1 hour for acute cardiovascular conditions. Chamber systems have coupled label-free detection with surface specific cell selection to avoid the use of labels at the detection stage. Most of these systems rely on samples, such as PBMCs, that are pre-purified (Ng S Y et al., "Label-free Impedance Detection of Low Levels of Circulating Endothelial Progenitor Cells for Point-of-Care Diagnosis", Biosensors and Bioelectronics, 2010, 25, 1095-1101). However, their reliance on surface specific capture is limiting, since the much more abundant red blood cells can mask the access of the surfaces for the other cells.

Conventional preparation methods for PBMCs are based on the different in size and density in comparison to their counterparts, such as the red blood cells. For cell-based detection, it is not necessary to separate the other constituents (such as plasma) from the cells, although the techniques used usually do.

There are a number of conventional methods for preparing PBMCs, with the most popular method being centrifugation where the cells are recovered in a buffy coat layer in specific tubes containing different density portions after the centrifugation procedure. The blood samples required are usually in the order of milliliters (ml), and are drawn by syringes and require lab facilities for preparation. Therefore, the preparation of PBMCs off-chip drastically diminishes the interest of using microfluidic devices for point-of-care applications, which need to handle small volumes (for example a blood sample from a finger prick is about 50 µl), at the patient's side.

The concept of centrifugation has also been used on chips to provide pumping of samples through channels and chambers. It is also applied to the separation of cells and other blood constituents (Kang D-R et al., "Blood micro-separator", US2006/0263265), but requires a rotation mechanism and complex integration schemes for detection.

Size filtration using porous membranes, either microfabricated (Siyang Zheng et al., "Membrane microfilter device for selective capture, electrolysis and genomic analysis of human circulating tumor cells" Journal of Chromatography A, 2007, 1162, 154-161) or paper-like (Vona G. et al., "Isolation by Size of Epithelial Tumor Cells", American Journal of Pathology, 2000, 156 (1), 57-63; Illert W., "Methods of preparing peripheral stem cells from leukocytes reduction filters", EP1484390), has been used for the preparation and detection of rare circulating cells (mostly CTCs). In these systems, the sample is passed through a membrane containing pores of specific sizes that will let the small cells (eg. red blood cells) go through, while retaining bigger cells (eg. CTCs and/or white blood cells). The efficiencies achieved are relatively high and the cells are analyzed directly on the membranes, either by optical or biomolecular inspection. However, such techniques cannot be easily integrated in a label-free point-of-care system, which require counting of cells on the membranes or transferring the lysed samples to a specific detector, such as a real-time PCR machine, which does not provide accurate levels.

Size filters have also been microfabricated in completely sealed systems (Maltezos G. et al., "Fluorescence detector, filter device and related methods", US2008/0013092; Battrell C. F. et al., "Method and system for microfluidic manipulation, amplification and analysis of fluids, for example, bacteria assays and antiglobulin testing", U.S. Pat. No. 7,416,892). However, the systems are usually used to trap big unwanted particles and detect small (molecules) species. Another drawback of these systems lies in the planar fabrication technologies (mainly silicon processes) which drastically reduce the area of trapping in the systems.

SUMMARY

According to an embodiment, a microfluidic system for detecting a biological entity in a sample volume is provided. The microfluidic system may include: a chamber configured to receive the sample volume, wherein the chamber comprises a detection region for detecting the biological entity; a first port in fluid communication with the chamber; and a second port comprising a filter in fluid communication with the chamber; and wherein a fluid provided to the first port or the second port flows between the first port and the second port through the chamber.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION

Figure 1A:
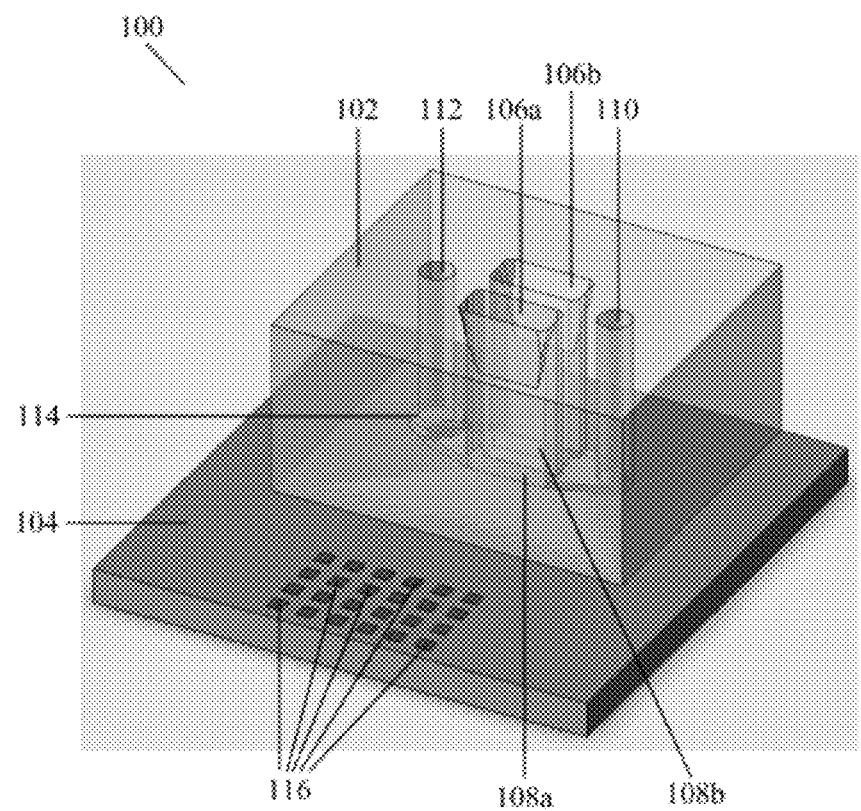
FIGS. 1A to 1C show perspective views of a microfluidic system, according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Various embodiments may provide a microfluidic system and a method for detecting biological entities, such as cells or biomarkers, with relatively improved performance and efficiency, without or with reduced at least some of the associated disadvantages of the current systems.

Various embodiments may provide a microfluidic system and a method for the detection biological entities, such as cells or biomarkers, and for example peripheral blood mononuclear cells (PBMCs) or circulating endothelial progenitor cells (EPCs), from relatively small volumes of blood samples. In various embodiments, the microfluidic system may include an open chamber for the detection of the biological entities. The microfluidic system may be provided on or in a microchip to form a microfluidic chip with an integrated open chamber.

Various embodiments may provide an integrated microfluidic system for the label-free detection of peripheral blood mononuclear cells (PBMCs) or circulating endothelial progenitor cells (EPCs) in the blood of patients, so as to provide an integrated bedside diagnostic test. The microfluidic system may provide the functions of sample preparation, for example isolating peripheral blood mononuclear cells (PBMCs) or circulating endothelial progenitor cells (EPCs) from the blood samples, specific cell capture based on antibody-antigen recognition and relatively highly sensitive label-free impedance detection, in a relatively compact system.

In various embodiments, the microfluidic system may provide the functions of preparing cells, e.g. PBMCs or EPCs, from a relatively small whole blood sample and detecting the cells. The preparation of the cells may include isolating, enriching or concentrating the cells to be detected.

Various embodiments may provide a sample-to-answer integrated system including a microfluidic chip to detect PBMCs or EPCs from a whole blood sample. Samples may be loaded into the system and information or an answer may be projected based on the sample in a relatively short time. The integrated system may be based on a label-free impedance spectroscopy-based detection platform that may be able to detect relatively small number of cells. The PBMCs or EPCs may be isolated from other blood cells and transferred to the open chamber for detection. The system may filter out other blood cells based on the size difference of the PBMCs, the EPCs and other blood cells. In various embodiments, specific cells, such as EPCs, may be magnetically labelled, for example with magnetic beads, for further isolation and concentration. This may help to magnetically isolate the magnetically labelled EPCs from the PMBCs in order to detect the EPCs.

Various embodiments may provide a method and a microfluidic system for obtaining a solution of PBMCs or EPCs from a relatively small blood sample (<100 μl), with a high efficiency, and integrated with an open chamber for detection of specific cell sub-types, such as the PBMCs or EPCs, and to minimise rare cell loss. Various embodiments may provide sample-to-answer results in a point-of-care enabled system with minimal fluidics, using label-free detection.

Various embodiments may provide a microfluidic system and a method that provide preparation and detection of cells, such as PBMCs or EPCs or other cell types with distinguishable surface markers, in a chamber in a single microfluidic chip that may allow label-free detection of the cells. The PBMCs or EPCs or other cell types may be in a solution of whole blood.

Various embodiments may provide a microfluidic system and a method to prepare a PBMC or an EPC sample purified from a whole blood sample within an open chamber in a microfluidic chip. The microfluidic system may be integrated with a label-free detection technique to provide a detection region close to the sample preparation region. The detection region may include a capture surface functionalized with specific capture molecules. The integration of cell preparation, filtration and detection in an open chamber in a microfluidic chip of various embodiments eliminates the need for a transferring process, for example between different modules for filtration and detection, thereby minimising cell loss, for example at the interconnections or along the walls of microchannels, during the sampling procedure. The microfluidic system may include a membrane having a pore size of about 3 μm to about 8 μm for filtration purposes. The membrane filter may be integrated with the microfluidic system to provide an integrated approach based on size separation. The membrane filter may provide a relatively large filtration area and a relatively high cell recovery efficiency.

Various embodiments may provide a method and a microfluidic system with an open chamber including a detection region, for detection of a biological entity in a sample volume, where the sample volume may be directly loaded into the open chamber of the microfluidic system from the top opening of the open chamber. This eliminates the need for a transferring process or flow-through fluidics to transfer the biological entity to the detection region, thereby minimising cell loss, for example at fluidic interconnections. In various embodiments, small sample volumes may be used along with sequential batch loading into the open chamber of the microfluidic system.

In various embodiments, the sample may be purified by passing the sample through a filter, such as a membrane filter, in the microfluidic system in order to isolate and retain the biological entity to be detected, for example PBMCs or EPCs, by the filter while removing any biological entity not to be detected which pass through the filter. The biological entity (eg. PBMCs or EPCs) to be detected is then removed from the filter and transferred to the chamber where detection may be performed.

In various embodiments, a detection region may be provided at the bottom of the open chamber, having a capture surface functionalized with specific capture molecules. The capture surface may be linked to any sensors or detectors that may detect the presence of a biological entity. The microfluidic system may further include two ports in fluid communication with the chamber or the capture surface. The two ports may be coupled or connected to the chamber by relatively short microchannels such that a fluid, such as a buffer solution may be provided to the open chamber via either of the ports for sample processing and washing of the detection region. The two ports may be coupled to pumps or syringes to move the buffer solution along the fluidic microchannels and the chamber. For example, the pumps may be used to input the buffer solution into the microfluidic system or to extract the sample and/or the buffer solution from the microfluidic system.

In various embodiments, a fluid, such as a buffer solution, may be passed through the chamber containing the sample with the biological entity to be detected to flow the sample through the filter, thereby retaining the biological entity to be detected at the filter while removing the biological entity not to be detected and the buffer solution to waste. A backflow of a fluid, such as a buffer solution, may be flowed through the filter in the opposite direction to remove and transfer the biological entity to be detected as retained at the filter to the chamber, the detection region of the chamber or the microelectrode array within the chamber. In various embodiments, capture molecules may be provided and/or attached on the surface of the microelectrode array to capture the biological entity to be detected. The capture molecules may be antibodies specific to the biological entity to be detected. In various embodiments, the microelectrode array may be configured to generate non-uniform electric fields to induce dielectrophoresis to assist in the capture and incubation of the biological entity to be detected.

In various embodiments, the microfluidic system may further include a movably arranged magnetic element configured to provide or generate a magnetic field in a vicinity of the detection region or the microelectrode array. The magnetic element may be a permanent magnet or an electromagnet. The generated magnetic field may help to trap the biological entity that has been magnetically labelled at the detection region or the microelectrode array. In further embodiments, a plurality of magnets may be provided such that two magnets, three magnets or four magnets may be provided.

In various embodiments, the biological entity may be trapped at the detection region of the microfluidic system by capture molecules, dielectrophoresis or magnetic field or any combination thereof.

Various embodiments may provide surface marker identification. This may be achieved by providing specific capture molecules, such as antibodies. For example, antibodies specific to epithelial cell adhesion molecule (EpCAM) of CTCs or CD34 or CD133 protein or the endothelial marker protein, VEGFR2/KDR, of EPCs may be provided. Further embodiments may provide multiple marker separation. For example, a first antibody may be coupled to the cells of interest and provided for magnetic trapping while a second antibody specific to the cells of interest may be functionalized on the surfaces of the electrodes. After removal of other cells not of interest, for example after a washing process, only specific cells coupled with both the first and second antibodies would remain on the electrodes.

Various embodiments may provide a method and a microfluidic system for integrated cell detection for relatively rapid separation of rare endothelial progenitor cells (EPCs) in small volumes of whole blood (<100 μl), as well as their selective capture or immobilization and their detection by immunochemistry coupled with electrochemical impedance sensing on a localised detection region, such as on a microelectrode array (MEA). The whole blood samples may be blood samples from a finger prick of a patient. Various embodiments may allow the potential to detect EPC as low as 0.1% of peripheral blood mononuclear cells (PBMCs) directly from small-sized blood samples in a lab-on-chip setting. This may provide a screening test, a bedside monitoring system or a point-of-care application for healthcare monitoring, drug therapy optimization and stent implant decision making. Various embodiments may allow the overall detection time to be within 1 hour so that timely information could be provided to the doctors for making fast treatment decisions, particularly in urgent situations. Such a relatively fast separation process, cell surface marker identification, as well as spatial enrichment and arrangement of the target cells (eg. EPCs) may enable a wide range of cell-based applications to be performed in micro total analysis systems (μTAS).

Various embodiments may provide a method and a microfluidic system for the lysis of red blood cells (RBCs) with immunomagnetic separation. The blood sample containing EPCs and RBCs may be initially prepared and mixed with a lysis buffer solution of chemicals, including ammonium chloride ($NH_4Cl$) for lysis effect (ie. $NH_4Cl$ as a lysing agent), sodium bicarbonate (NaHCO$_3$) as a pH buffer and ethylenediaminetetraacetic acid (EDTA) as an anti-coagulant. In various embodiments, the sodium bicarbonate in the lysis buffer solution may also function as a blocker to cease Na+-K+-ATPase. The lysis buffer solution may further include magnetic elements, such as magnetic beads. The magnetic beads may be antibody-linked magnetic beads (ie. magnetic beads coupled with antibody) for coupling to the EPCs which may aid the selective capture of the EPCs and detection by immunochemistry in the microfluidic system of various embodiments. In various embodiments, selective cell lysis, such as lysis of RBCs, may occur in the solution containing the EPCs. However, no lysis of the EPCs may occur. Such a preparation process simultaneously perform removal of red blood cells (RBCs) and cell surface marker labeling in a relatively short time, requiring about 10 minutes, and may result in the completion of the preparation and detection processes in less than 1 hour. Various embodiments may result in relatively higher efficiency after lysis (>90% EPCs).

In various embodiments, the lysis buffer solution may include approximately 150 mM NH$_4$Cl, 10 mM NaHCO$_3$, 0.1 mM EDTA and about 2000 magnetic beads. However, it should be appreciated that the concentration of NH$_4$Cl may be in the range of about 10 mM to about 150 mM, for example a range of about 10 mM to about 100 mM, a range of about 10 mM to about 50 mM or a range of about 50 mM to about 150 mM, such that the concentration of NH$_4$Cl may be about 10 mM, about 20 mM, about 50 mM, about 100 mM, about 120 mM or about 150 mM. It should be appreciated that the concentration of NaHCO$_3$ may be in the range of about 10 mM to about 100 mM, for example a range of about 10 mM to about 50 mM or a range of about 10 mM to about 20 mM, such that the concentration of NaHCO$_3$ may be about 10 mM, about 20 mM, about 30 mM, about 50 mM, about 80 mM or about 100 mM. It should also be appreciated that the concentration of EDTA may be in the range of about 0.01 mM to about 1.0 mM, for example a range of about 0.01 mM to about 0.5 mM, a range of about 0.01 mM to about 0.1 mM or a range of about 0.1 mM to about 1.0 mM, such that the concentration of EDTA may be about 0.01 mM, about 0.05 mM, about 0.1 mM, about 0.2 mM, about 0.5 mM or about 1 mM.

In various embodiments, the blood sample may be mixed with the lysis buffer solution such that the volume ratio of NH$_4$Cl (having a concentration of about 150 mM) to blood ranges from 1:1 to 1:10. In various embodiments, the total volume of the mixture solution may be less than 100 µl.

It should be appreciated that the number of magnetic beads may be different in various embodiments, depending on the number of cells to be coupled with the magnetic beads. In various embodiments, a ratio of 2 magnetic beads per 1 cell is provided. For example, in an approximately 20 µl blood sample, the number of EPCs may be in the range of about 0.1-1% of PMBCs, corresponding to about 100-1000 EPCs. Therefore, approximately 2000 magnetic beads may be required. In further embodiments, a relatively higher ratio of magnetic beads per 1 cell may be provided. Depending on the size of the magnetic beads (for example micron-sized magnetic beads or nanometer-sized magnetic beads), approximately 2000-20000 magnetic beads may be provided.

Various embodiments may provide a method and a microfluidic system for the relatively rapid separation and detection of rare endothelial progenitor cells (EPCs), based on the selective lysis of red blood cells (RBCs) and immunomagnetic enrichment to separate the EPCs, such as the CD34+ cells, from the blood. A sample containing CD34+ cells may be prepared and mixed with a solution containing NH$_4$Cl, NaHCO$_3$, EDTA and antibody-linked magnetic beads. The solution may help in lysing or eradicating the RBCs in the sample while also labeling the antibody-linked magnetic beads onto the CD34+ cell markers simultaneously in a relatively short time of about 10 minutes. Such a timeframe satisfies the requirement for CD34+ detection. After incubation of the sample, the sample containing the CD34+ cells and the mixture solution may be loaded or provided to the microfluidic system of various embodiments. The microfluidic system may filter the sample to concentrate and enrich the CD34+ cells by removing other cells which are not of interest. Subsequently, a localised magnetic field may be applied to the vicinity of the microelectrode area at the detection region to selectively isolate and concentrate the immunomagnetically labelled CD34+ cells, which are coupled with magnetic beads, onto the microelectrode, thereby trapping and immobilizing the CD34+ cells on the microelectrode, for detection and quantitative measurements. This helps to specifically extract the CD34+ cells from the blood sample while other remaining cells, such as un-lysed RBCs and PBMCs, which do not express CD34 antigen, may be removed from the sample by washing them away.

Various embodiments may provide a label-free detection method. Such a label-free detection method may employ impedance measurement or impedance spectroscopy, as described in WO2010/050898 filed 1 Sep. 2009, which disclosure is incorporated herein by reference. For this detection mechanism, the capture surface within the open chamber is patterned with gold electrodes on a microchip, which are linked or in electrical communication with a measurement or detection system. The electrodes may be provided as a microelectrode array. The electrodes may be specifically provided with capture molecules, such as antibodies, for specific targeted cells or biological entities, while the remaining portions of the microchip not covered by the electrodes may be passivated with a repellent material, for example polyethylene glycol (PEG). The electrodes may also be used to perform dielectrophoresis (DEP) to attract and concentrate the cells on the electrodes to accelerate cell capture and increase efficiency.

In various embodiments, other detection mechanisms may be used and the detection region may be correspondingly modified or provided in suitable forms based on the detection mechanism. For example, refractive index-based sensing mechanisms like surface plasmon resonance (SPR), or optical ring resonators, or interferometers, may be used as the detection mechanism, where the capture surface may be patterned with a gold layer containing spots of capture molecules, such as antibodies. Light may be channeled to the capture area using photonics or by direct illumination. Localised SPR may also be possible.

Another possible detection mechanism may use field-effect sensors, such as silicon nanowire arrays, which may be provided and patterned on the capture surface and functionalized with specific capture molecules, such as antibodies. The silicon nanowire arrays may be linked to a measurement system to measure the resistance of the silicon nanowire arrays, which may change when a biological entity, such as a cell, is captured on the surface.

Conventional fluorescence measurements may also be used for the detection of the biological entity. The captured cells may be stained with various dyes that may be excited using an external light source and the emission may be detected by, for example, a charge-coupled device (CCD) camera or a photomultiplier tube (PMT).

In further embodiments, a shear flow controlled washing protocol may be carried out by flowing a fluid, such as a buffer solution, through the microelectrode array and the chamber to assist specific cell selection on the microelectrode electrode and remove any biological entity not to be detected that may be present.

Various embodiments may alleviate the challenge of sample loss during transfer between different systems or sample being lodged at interfaces between different systems by providing a microfluidic system in a single microfluidic package or a microfluidic chip which provides sample preparation and detection in a chamber. The chamber may be an open chamber that may provide a small sensing area for high sensitivity sensing and provide a relatively high efficiency level of cell recovery through the detection process.

Various embodiments may provide a microfluidic system based on the fluidic motion or flow in the microchannels and the chamber from a section of the microfluidic system to another section, thereby allowing seamless integration with label-free detection.

Various embodiments may provide a microfluidic system which advantageously does not require a separate sample preparation module or system or a rotation mechanism for centrifugation.

Various embodiments may provide diagnostics for cells, such as the detection of peripheral blood mononuclear cells (PBMCs) or rare circulating cells, for example EPCs, label-free detection for hands-free integrated system with high sensitivity, an automated system with processing at relatively low cost and diagnosis, prognosis and therapy monitoring, for example for cancers, cardiovascular diseases and graft monitoring.

Various embodiments may provide bedside or point-of-care (POC) processing and detection, in less than 1 hour, of biological entities, such as rare circulating tumour cells (CTCs), such as endothelial progenitor cells (EPCs), from relatively small blood samples (<100 μl) for diagnostic purposes. Various embodiments may provide an integrated microfluidic system for the label-free detection of EPCs in the blood of patients, so as to provide an integrated bedside diagnostic test for integrated sample to answer results, with samples obtained from one or more finger pricks (each finger prick about 50 μl of blood) from the patients. The microfluidic system may provide the functions of sample preparation, from the blood samples, specific cell capture based on antibody-antigen recognition and relatively highly sensitive label-free impedance detection (for example about 0.1% EPC in a PBMC sample), in a relatively compact system. This may help, for example, in the decision making process on the type of stent for use in a patient, such as a heart attack patient.

In various embodiments, the microfluidic system and method may provide detection of cells with relatively high sensitivity, relatively higher throughput and at relatively low cost. The microfluidic system may include silicon chips and plastic fixtures.

Various embodiments may provide a microfluidic system including an open chamber and a method to separate white blood cells, including circulating cells, based on the difference in the size of different cells or biological entities within the open chamber.

The microfluidic system of various embodiments may be produced at a relatively low cost and may be disposable.

In the context of various embodiments, the term "microfluidic system" may mean a fluidic system including one or more channels in the micrometer range (which may also be referred to as microchannels) where a sample volume may be provided to flow in and along the microchannels based on fluidic motion. In various embodiments, the microfluidic system may be formed on a microchip to form a microfluidic chip.

In the context of various embodiments, the term "detection region" may mean a region where a biological entity may be detected. In various embodiments, the detection region may be provided in a chamber, for example at the bottom of the chamber. In various embodiments, the chamber may be an open chamber. Detection may be carried out based on label-free detection method, for example impedance measurement or sensing. The detection region may include an electrode, a pair of electrodes or a microelectrode array including more than one electrode or more than one pair of electrodes. Each pair of electrodes may include an inner electrode and an outer electrode having a complementary shape that substantially surrounds the inner electrode. In various embodiments, the electrode, pair of electrodes or the microelectrode array may be positioned at the bottom of the detection region. In various embodiments, the biological entity may be trapped at the detection region by means of dielectrophoresis or capture by capture molecules, for example antibodies. The capture molecules may be provided and/or attached on the surfaces of the electrode or electrodes.

In the context of various embodiments, the term "open chamber" may mean a chamber or a channel where a solution may flow or pass through or remain in the chamber or channel. In various embodiments, the open chamber has a top opening. In other words, the open chamber does not have a top cover. In various embodiments, the term "chamber" may mean an "open chamber".

The term "in fluid communication" in relation to the different sections of a microfluidic system may mean a communication between two sections of the microfluidic system. In various embodiments, this communication may be a direct connection or a direct path between two sections of the microfluidic system or may include one or more intervening sections in the path between two sections of the microfluidic system.

In the context of various embodiments, the term "port" may mean an opening, a recess or a cavity providing a means for the passage of fluid. In various embodiments, the microfluidic system may include at least two ports in fluid communication with the chamber. The microfluidic system may include an inlet port providing a means of entrance or intake. The microfluidic system may include an outlet port providing a means of exit or output. In various embodiments, each port may have a hollow cylindrical structure. The hollow cylindrical structure may be a single continuous structure. In various embodiments, the hollow cylindrical structure may have a length in the range of about 1 mm to about 3 mm, for example a range of about 1 mm to about 2 mm or a range of about 1.5 mm to about 3 mm, such that the length may be about 1 mm, about 1.5 mm, about 2 mm, about 2.5 mm or about 3 mm. In various embodiments, the hollow cylindrical structure may have a diameter in the range of about 0.6 mm to about 1.5 mm, for example a range of about 0.6 mm to about 1 mm or a range of about 1 mm to about 1.5 mm, such that the diameter may be about 0.6 mm, about 0.66 mm, about 0.8 mm, about 1.0 mm or about 2.5 mm. In further embodiments, each port having a hollow cylindrical structure may include a first and second portions, having the dimensions of approximately 0.66 mm (diameter)×1.5 mm (height) and approximately 1.5 mm (diameter)×1.5 mm (height), respectively. The first portion may be on top of the second portion or vice versa. However, it should be appreciated that each port or each portion of each port may have a different structure or configuration and may have a different dimension. In various embodiments, a third or more ports in fluid communication with the chamber may be provided, having suitable structures, configurations and dimensions.

In various embodiments, the term "biological entity" may mean a biomarker, a cell, an organelle, a virus particle, a biopolymer or a combination thereof. The term "cell" may include a eukaryotic cell or a prokaryotic cell. The term "cell" may also include a peripheral blood mononuclear cell, a cell of the immune system including a white blood cell, a T cell and a T helper cell, a biomarker including a circulating tumour cell, a lymphocyte, a CD4 lymphocyte and an endothelial progenitor cell. The term "eukaryotic cell" may include a mammalian cell or a yeast cell. The term "mammalian cell" may include a tumour cell, a blood cell, a cell of the immune system, a progenitor cell and a fetal cell. The term "biopolymer" may include a polypeptide, a nucleic acid, a lipid and an oligosaccharide. In various embodiments, the biological entity may have a DNA anchor for incubation and capture on the surface of the microelectrode array.

In various embodiments, the sample volume may be a blood sample volume. The blood sample volume may be a whole blood sample volume.

In various embodiments, the chamber or the open chamber may have a volume in the range of about 1 μl to about 500 μl, for example a range of about 1 μl to about 300 μl, a range of about 1 μl to about 200 μl, a range of about 1 μl to about 100 μl, a range of about 1 μl to about 50 μl, a range of about 1 μl to about 20 μl, a range of about 200 μl to about 500 μl, a range of about 50 μl to about 500 μl or a range of about 50 μl to about 200 μl, such that the chamber may have a volume of about 2 μl, about 5 μl, about 10 μl, about 20 μl, about 50 μl, about 100 about 200 μl, about 300 μl or about 500 μl.

In various embodiments, the detection region may include a microelectrode array, which may include one or more pairs of electrodes, such as two pairs of electrodes, four pairs of electrodes, six pairs of electrodes, eight pairs of electrodes, twelve pairs of electrodes, sixteen pairs of electrodes or twenty four pairs of electrodes and which may be arranged in a 2×1 array, a 1×4 array, a 2×2 array, a 1×6 array, a 2×3 array, a 3×2 array, a 2×4 array, a 4×2 array, a 2×6 array, a 4×3 array, a 2×8 array, a 4×4 array, a 4×6 array or a 3×8 array. Each pair of the electrodes may include an inner electrode and an outer electrode having a complementary shape that substantially surrounds the perimeter of the inner electrode. In various embodiments, the electrodes may be made of gold, titanium, platinum or other metals or conductive materials.

In various embodiments, the inner electrodes may be disc-shaped electrodes while the outer electrodes may be horse-shoe-shaped electrodes. However, it should be appreciated that the inner electrodes may be of any shape, for example a triangular shape, an oval shape, a square shape, a rectangular shape or a diamond shape and the outer electrodes may be in the form of a narrow strip having a complementary shape that substantially surrounds the perimeter of the corresponding inner electrodes. The inner electrodes may be the working electrodes and the outer electrodes may be reference electrodes. In various embodiments, the outer electrodes may be shorted together to provide a relatively bigger surface area to increase sensitivity, while the inner electrodes may be controlled individually for relatively high sensitive impedance measurements or shorted together to generate a non-uniform electric filed that induces dielectrophoresis (DEP). In various embodiments, specific capture molecules may be provided and/or attached on the surface of the microelectrode array.

Dielectrophoresis, as known in the art, is a technique often used for separating microparticles, by inducing a varying spatially non-uniform electrical field (dielectrophoretic field) that generates unequal electrical polarization dipoles in a neutral dielectric particle, including for example a cell, thereby resulting a dielectrophoretic force.

The dielectric properties of the medium surrounding a particle may affect the dielectrophoretic force experienced by the particle. A particle that is more polarisable than its surrounding medium will experience a net force toward high electric field regions (positive DEP), while a particle that is less polarisable than its surrounding medium will experience a net force toward low electric field regions (negative DEP).

In various embodiments, the electric field generated for the dielectrophoretic trapping of may have an electric field minimum occurring at the centres of the inner electrodes, thereby directing the cells towards the capture molecules. In various embodiments, the dielectrophoretic field generated may be a negative dielectrophoretic field such that the target biological entity may be concentrated at the electrical field minima occurring at the centre of the inner electrodes, thereby enhancing impedance detection sensitivity without the need for labelling of the sample.

In various embodiments, the electrical signal applied to the microelectrode array to induce the dielectrophoretic field may have a peak-to-peak amplitude in the range of about 0.1 V to about 20 V, for example a range of about 0.1 V to about 10 V, a range of about 0.1 V to about 5 V, a range of about 0.1 V to about 1.5 V, a range of about 1.5 V to about 10 V or a range of about 1.5 V to about 20 V, such that the electrical signal may have a peak-to-peak amplitude of about 0.1 V, about 0.5 V, about 1.0 V, about 1.5 V, about 5 V, about 10 V or about 20 V. In various embodiments, the frequency of the electrical signal applied to the microelectrode array to induce the dielectrophoretic field may be in the range of about 10 kHz to about 100 MHz, for example a range of about 10 kHz to about 50 MHz, a range of about 10 kHz to about 10 MHz, a range of about 10 kHz to about 1 MHz, a range of about 1 MHz to about 100 MHz or a range of about 10 MHz to about 100 MHz, such that the frequency of the electrical signal may be about 10 kHz, about 100 kHz, about 1 MHz, about 5 MHz, about 10 MHz, about 20 MHz, about 50 MHz or about 100 MHz. In various embodiments, the electrical signal applied to the microelectrode array to induce the dielectrophoretic field may have a peak-to-peak amplitude of about 1.5 V and a frequency of about 1 MHz.

In various embodiments, in order to obtain a high sensitivity at the detection region, a relatively small sensor electrode or a microelectrode array may be arranged on the detection region. In various embodiments, each electrode may have a dimension of about 100 μm.

In various embodiments, the filter may be a paper filter, fiber meshes, a polymer filter or a functional filter having coated antibodies or charges. In various embodiments, the filter may be made of parylene, polystyrene, polyethylene, polymethylmetacrylate (PMMA) or polydimethylsiloxane (PDMS). In various embodiments, the filter may be a membrane filter. In an embodiment, the filter may be a Sterlitech polycarbonate membrane.

In various embodiments, the filter may have dimensions in terms of diameter in the range of about 2 mm to about 4 mm, for example a range of about 2 mm to about 3 mm, such that the diameter of the filter may be about 2 mm, about 3 mm or about 4 mm. The filtering area of the filter may have substantially the same dimensions as that of the filter. In various embodiments, the filter may have pore sizes in the range of about 3 μm to about 50 μm, for example a range of about 3 μm to about 30 μm, a range of about 3 μm to about 20 μm, a range of about 3 μm to about 10 μm, a range of about 5 μm to about 50 μm, a range of about 10 μm to about 50 μm or a range of about 10 μm, to about 30 μm, such that a filter having a pore size of about 3 μm, about 5 μm, about 8 μm, about 10 μm, about 15 μm, about 20 μm, about 30 μm, about 40 μm or about 50 µm, may be provided. However, it should be appreciated that the filter may have any pore size, depending on the biological entity or cell to be filtered or allowed to pass.

In various embodiments, the microchannels of the microfluidic system coupling the first port to the chamber or the second port to the chamber may have a width in the range of about 50 µm to about 200 µm, for example a range of about 50 µm to about 100 µm or a range of about 100 µm to about 200 µm, such that the microchannel may have a width of about 50 µm, about 100 µm, about 150 µm or about 200 µm. In various embodiments, the microchannel may have a height in the range of about 20 µm to about 100 µm, for example a range of about 50 µm to about 100 µm, a range of about 20 µm to about 50 µm or a range of about 20 µm to about 30 µm, such that the microchannel may have a height of about 20 µm, about 40 µm, about 60 µm, about 80 µm or about 100 µm.

In various embodiments, the filtering flow rate or the flow rate at which the sample and a fluid (eg. a buffer solution) are passed through the filter to retain the biological entity of interest at the filter and filtering other biological entities, may be in the range of about 3 µl/minute to about 600 µl/minute, for example a range of about 3 µl/minute to about 400 µl/minute, a range of about 3 µl/minute to about 200 µl/minute, a range of about 50 µl/minute to about 600 µl/minute, a range of about 50 µl/minute to about 400 µl/minute, a range of about 100 µl/minute to about 200 µl/minute or a range of about 200 µl/minute to about 400 µl/minute, such that the filtering flow rate may be about 3 µl/minute, about 10 µl/minute, about 30 µl/minute, about 50 µl/minute, 100 µl/minute, about 200 µl/minute, about 300 µl/minute, about 400 µl/minute, about 500 µl/minute or about 600 µl/minute.

In various embodiments, the backflow rate or the flow rate at which a fluid (eg. a buffer solution) is passed through the filter in the opposite direction to the filtration process to remove the retained biological entity at the filter, may be in the range of about 200 µl/minute to about 1000 µl/minute, for example a range of about 200 µl/minute to about 800 µl/minute, a range of about 200 µl/minute to about 600 µl/minute or a range of about 400 µl/minute to about 800 µl/minute, such that the backflow rate may be about 200 µl/minute, about 400 µl/minute, about 600 µl/minute, about 800 µl/minute or about 1000 µl/minute.

In various embodiments, the washing rate or the flow rate at which a fluid (eg. a buffer solution) is passed through the first port or the second port to remove other non-specific biological entities, may be in the range of about 15 µl/minute to about 400 µl/minute, for example a range of about 15 µl/minute to about 300 µl/minute, a range of about 15 µl/minute to about 200 µl/minute, a range of about 50 µl/minute to about 400 µl/minute, a range of about 50 µl/minute to about 300 µl/minute, a range of about 100 µl/minute to about 300 µl/minute or a range of about 100 µl/minute to about 200 µl/minute, such that the washing rate may be about 15 µl/minute, about 50 µl/minute, about 100 µl/minute, about 200 µl/minute, about 300 µl/minute or about 400 µl/minute.

In various embodiments, the biological entity of interest or the specific biological entity may be incubated on the surface of the microelectrode array for a duration in the range of about 5 minutes to 60 minutes (1 hour), for example a range of about 5 minutes to 40 minutes, a range of about 5 minutes to 20 minutes, a range of about 5 minutes to 10 minutes, a range of about 10 minutes to 60 minutes or a range of about 20 minutes to 60 minutes, such that the incubation duration may be about 5 minutes, about 10 minutes, about 20 minutes, about 30 minutes, about 40 minutes, about 50 minutes or about 60 minutes.

In various embodiments, a method for manufacturing a microfluidic system for detecting a biological entity in a sample volume is provided. The method may include providing a chamber configured to receive the sample volume, wherein the chamber may include a detection region for detecting the biological entity; providing a first port in fluid communication with the chamber; and providing a second port including a filter in fluid communication with the chamber; and wherein a fluid provided to the first port or the second port flows between the first port and the second port through the chamber.

In various embodiments, a method for detecting a biological entity in a sample volume using a microfluidic system for detecting a biological entity in a sample volume, the microfluidic system including a chamber configured to receive the sample volume, wherein the chamber may include a detection region for detecting the biological entity; a first port in fluid communication with the chamber; and a second port comprising a filter in fluid communication with the chamber; and wherein a fluid provided to the first port or the second port flows between the first port and the second port through the chamber, is provided. The method may include providing the sample volume to the chamber; providing the fluid to the first port to pass the sample volume through the filter to retain the biological entity; removing the biological entity from the filter to the detection region of the chamber; and detecting the biological entity.

Figure 1B:
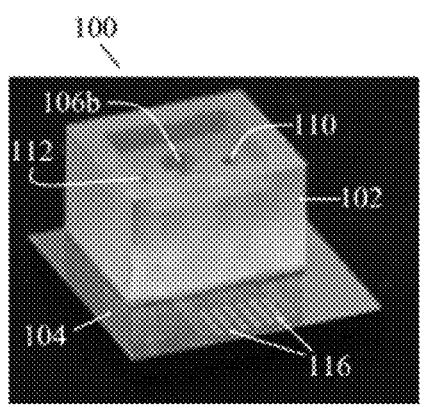
Figure 1C:
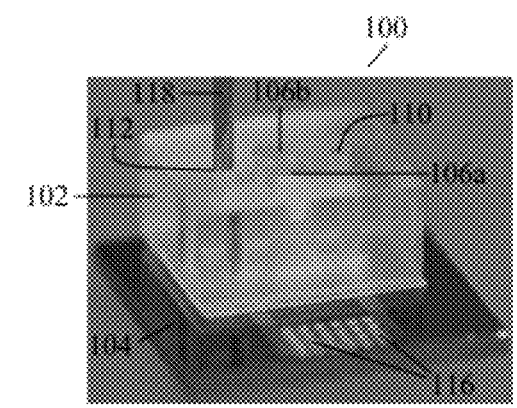

FIGS. 1A to 1C show perspective views of a microfluidic system 100, according to various embodiments. The microfluidic system 102 may be provided or integrated with a microchip 104 to form an integrated microfluidic system 100 for use in the preparation and detection of a biological entity in a sample volume, for example peripheral blood mononuclear cells (PBMCs) in a blood sample. The microchip 104 may be a silicon microchip. In various embodiments, the microfluidic system 102 may have the dimensions of approximately 7 mm×6 mm×3 mm. In various embodiments, the microchip 104 may have the dimensions of approximately 1 mm×1 mm×0.75 mm.

The microfluidic system 102 may include a pair of chambers 106a, 106b, configured to receive a sample volume. The chambers 106a, 106b, may be open chambers. In other words, a sample volume containing the biological entity that is to be detected, among other biological entities, is provided to the microfluidic system 102 of the integrated microfluidic system 100 via the chambers 106a, 106b. Each of the chambers 106a, 106b, may include a respective detection region 108a, 108b, having a respective capture surface, at the bottom of the respective chambers 106a, 106b, for detecting the biological entity. In various embodiments, the detection regions 108a, 108b, may include a microelectrode array (not shown), wherein the capture surfaces of the detection regions 108a, 108b, may be the surfaces of the microelectrode array. Capture molecules may be provided and/or attached on the surface of the microelectrode array to capture the biological entity of interest for detection. The capture molecules may be specific to the biological entity of interest for detection. In various embodiments, each of the chambers 106a, 106b, may be an open chamber.

The microfluidic system 102 may further include a first port 110 that may be connected to the chambers 106a, 106b such that the first port 110 may be in fluid communication with each of the chambers 106a, 106b, and a second port 112 that may be connected to the chambers 106a, 106b such that the second port 112 may be in fluid communication with each of the chambers 106a, 106b. The first port 110 and the second port 112 may be arranged substantially perpendicular to the capture surfaces of the detection regions 108a, 108b.

In various embodiments, the microfluidic system 102 may further include a filter 114 provided at the second port 112. The filter 114 may be integrated with the second port 112. The filter 114 may be a membrane filter. In various embodiments, the filter 114 may be provided in a horizontal configuration in the second port 112, or in other words, arranged horizontally in the second port 112.

In various embodiments, a microchannel (not shown) may be provided to couple the first port 110 to each of the chambers 106a, 106b. In various embodiments, a microchannel (not shown) may be provided to couple the second port 112 to each of the chambers 106a, 106b. In further embodiments, more than one microchannel, such as two microchannels, three microchannels or four microchannels, may be provided to couple the first port 110 to each of the chambers 106a, 106b, and more than one microchannel, such as two microchannels, three microchannels or four microchannels, may be provided to couple the second port 110 to each of the chambers 106a, 106b.

In various embodiments, the first port 110, the chambers 106a, 106b, and the second port 112 are in fluid communication with each other such that a fluid, for example a buffer solution, provided to the first port 110 or the second port 112 may flow between the first port 110 and the second port 112 through the chambers 106a, 106b. Accordingly, a fluid provided to the first port 110 may flow from the first port 110 to each of the chambers 106a, 106b and through each of the chambers 106a, 106b to the second port 112. Similarly in the opposite direction, a fluid provided to the second port 112 may flow from the second port 112 to each of the chambers 106a, 106b and through each of the chambers 106a, 106b to the first port 110.

In various embodiments, the integrated microfluidic system 100 may further include a plurality of contact pads 116 formed therein or thereon the microchip 104. The plurality of contact pads 116 may be in electrical communication with the microelectrode array provided at the detection regions 108a, 108b. The plurality of contact pads 116 may be connected to the microelectrode array via a plurality of electrical connections (not shown). In various embodiments, the number of the plurality of contact pads 116 may correspond to the number of the electrodes of the microelectrode array (not shown) at the detection regions 108a, 108b. In various embodiments, the plurality of contact pads 116 may be made of gold, titanium, platinum or other metals or conductive materials.

In FIG. 1C, there is shown a metal hollow pin 118 inserted into the second port 112 to act as the outlet. The metal hollow pin 118 is further connected to a tubing (not shown) for removing any sample.

In various embodiments, the microfluidic system 100 may further include a movably arranged magnetic element (not shown), for example a magnet, configured to provide or generate a magnetic field in the vicinity of the detection region 108a, 108b. The magnet may be positioned below the detection region 108a, 108b. The generated magnetic field may help to trap the biological entity that have been magnetically labelled at the detection region 108a, 108b. In various embodiments, the magnet may be a permanent magnet or an electromagnet.

In various embodiments, a third or more ports in fluid communication with the chambers 106a, 106b, may be provided to ease the filtering processes, by increasing the filtering area and the fluidic access. The third or more ports may or may not be provided with a filter.

In further embodiments, the filter 114 may be implemented in the vertical configuration in the second port 112, or in other words, arranged vertically in the second port 112, which may affect the flow pattern and provide certain advantages.

In alternative embodiments, only one chamber may be provided. In further embodiments, more than two chambers may be provided such that three chambers, four chambers or five chambers or even more chambers may be provided.

In various embodiments, the microfluidic system 102 may be made of polycarbonate, polyethylene, polymethylmetacrylate (PMMA) or polydimethylsiloxane (PDMS). In further embodiments, the microfluidic system 102 may be made of metal, for example aluminum or steel.

The operation of the microfluidic system 102, based on detection of the biological entity using impedance measurement, will now be described, by way of examples and not limitations.

The microfluidic system 102 may be used for the preparation and detection of peripheral blood mononuclear cells (PBMCs) in a blood sample. Preparation of the peripheral blood mononuclear cells (PBMCs) may mean concentrating the peripheral blood mononuclear cells (PBMCs) or filtering or isolating the peripheral blood mononuclear cells (PBMCs) from other cells or biological entities in the blood sample.

A buffer solution may initially be provided, directly, to the chambers 106a, 106b, before the blood sample is provided. The buffer solution may be provided to fill the entire volume of the chambers 106a, 106b, which may have a volume of about 4 μl. In alternative embodiments, the buffer solution may be provided to fill half the volume of the chambers 106a, 106b or provided sufficiently to cover or overlay the microelectrode array.

An impedance measurement may be taken as a background signal for normalization purposes. The buffer solution within the chambers 106a, 106b, may then be removed. However, it would be advantageous to maintain a certain volume of the buffer solution within the chambers 106a, 106b in order to dilute the subsequent blood sample provided to the chambers 106a, 106b, to ease processing and to minimize the occurrence of saturation, for example by red blood cells and other constituents or biological entities in the blood sample, at the detection regions 108a, 108b, which may prevent detection of the biological entity of interest that is to be detected. Therefore, prior to providing the blood sample to the chambers 106a, 106b, a certain volume of the buffer solution within the chambers 106a, 106b, may be removed, which may be about 2 μl, being half of the volume of the chambers 106a, 106b. The blood sample may then be provided to the chambers 106a, 106b. At this stage, the blood sample may contain a variety of biological entities, such as red blood cells, white blood cells and other cells, in addition to the PBMCs to be detected.

A filtration process may then be carried out. The sample, being the blood sample diluted with the buffer solution, may be extracted through the second port 112, for example by means of a pump attached to the second port 112, in order to pass the sample through the filter 114 and the second port 112 to waste. The entire volume of the sample may be removed or a certain volume of the sample within the chambers 106a, 106b, may be removed, for example about 2 μl. At this stage, the PBMCs may be retained at the filter 114 while the red blood cells may be removed to waste. As the second port 112 may generally be used to output the sample after passing through the filter 114, the second port 112 may also be defined as the outlet or the outlet port.

In various embodiments, the filtration process may be performed for a number of times, for example two times, three times or four times, to maximize the retention of PBMCs and remove other biological entities, for example the red blood cells, through the filter 114. Therefore, additional buffer solution may be provided through the first port 110, with the second port 112 closed, to fill the chambers 106a, 106b, and to further dilute the sample within. Further filtration may then be carried out by extracting the sample through the second port 112. A certain volume of the sample within the chambers 106a, 106b, may be removed through the filter 114 and the second port 112, to waste. In various embodiments, as the first port 110 may generally be used as an input means for the buffer solution, the first port 110 may also be defined as the inlet or the inlet port.

In various embodiments, during the filtration process, biological entities may be present on the capture surfaces of the detection regions 108a, 108b, located at the bottom of the chambers 106a, 106b, respectively. Therefore, incubation and dielectrophoresis, as part of the detection protocol, may be implemented during the filtration process to capture the PBMCs on the detection regions 108a, 108b.

At the end of the filtration process, most of the white blood cells or the PBMCs may be retained at the filter 114, while most of the red blood cells are removed to waste.

In order to recover the fraction of PBMCs from the cells retained at the filter 114 and to enable the capture and detection of the PBMCs, a buffer solution is provided through the second port 112, with the first port 110 closed, such that the direction of the liquid flow is reversed compared to that during the filtration process. In other words, a backflow or a reverse flow of the buffer solution through the second port 112 is performed, thereby removing the cells from the filter 114 and transferring the cells to the chambers 106a, 106b, such that the cells may be transferred to the detection regions 108a, 108b of the chambers 106a, 106b.

After the backflow of the buffer solution and the transfer of the cells to the chambers 106a, 106b, incubation and/or dielectrophoresis and washing, as part of the detection protocol, may be implemented to concentrate the cells at the detection regions 108a, 108b, for example at the microelectrode array of the detection regions 108a, 108b. During the washing process, a fluid may be flowed through the first port 110 and/or the second port 112 to remove non-specific biological entities that are not captured on the surface of the microelectrode array. Subsequently, detection of the PBMCs at the detection regions 108a, 108b, of the chambers 106a, 106b, may be carried out. The PBMCs may be detected using a label-free detection method, such as impedance measurement.

In various embodiments, the backflow process may be repeated after capture of the PBMCs at the detection regions 108a, 108b to increase the recovery efficiency. In various embodiments, the backflow process may be performed for a third time or a fourth time, each time after capture of the PBMCs at the detection regions 108a, 108b.

Accordingly, in various embodiments, a fluid, such as a buffer solution, provided to the first port 110 may be configured to flow through the chambers 106a, 106b, and the filter 114 such that the biological entity is retained by the filter 114 and a fluid, such as a buffer solution, provided to the second port 112 may be configured to flow through the filter 114 such that the biological entity is removed from the filter 114 to the chambers 106a, 106b, for capture by the capture molecules attached to the surface of the microelectrode array.

In various embodiments, it may also be possible to implement a sequential batch processing protocol, where different volumes of the blood samples may be processed sequentially.

After the processing procedures, detection of the PBMCs captured on the microelectrode array may be performed.

Figure 2:
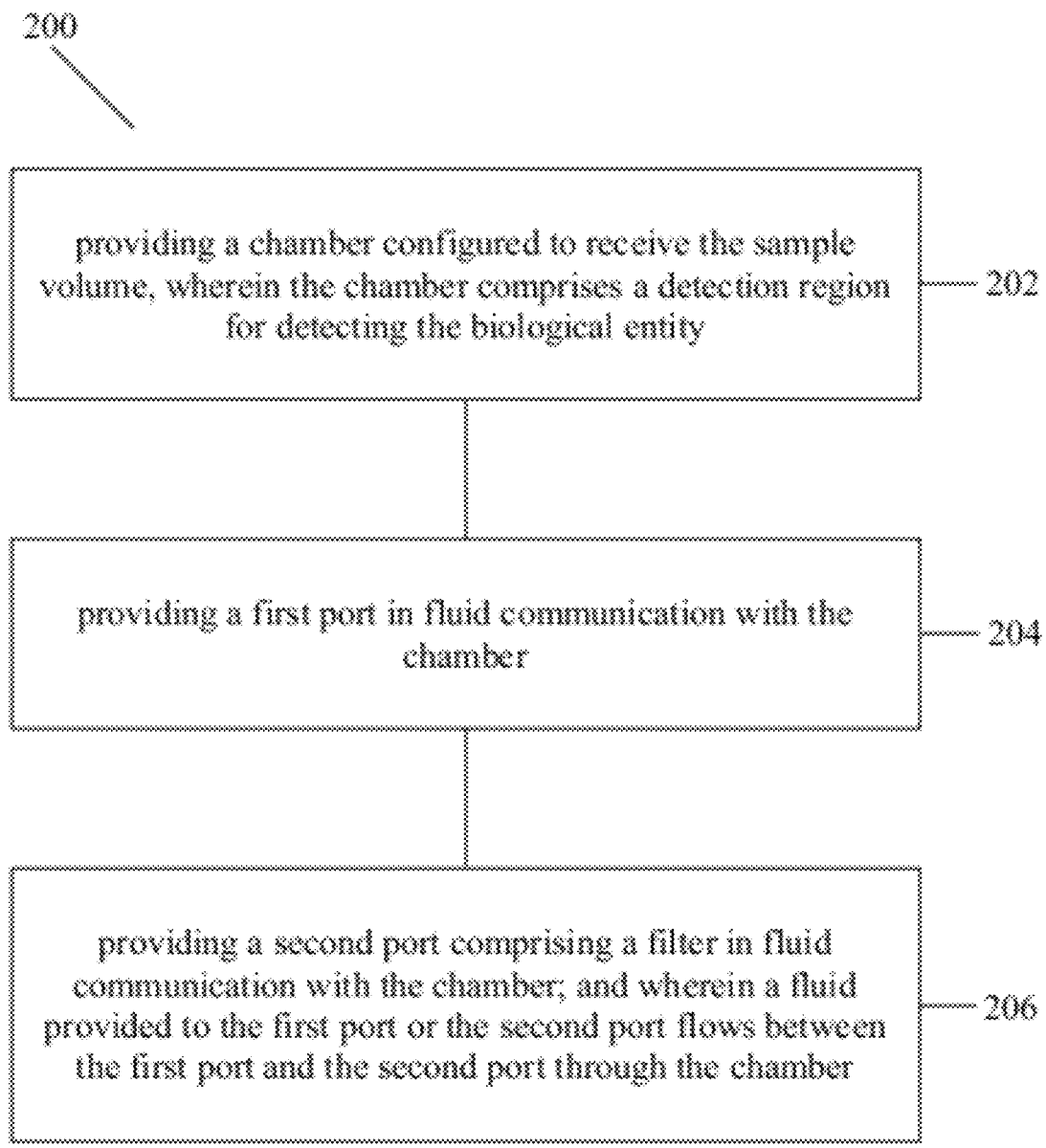
FIG. 2 shows a flow chart illustrating a method for manufacturing a microfluidic system, according to various embodiments.

FIG. 2 shows a flow chart 200 illustrating a method for manufacturing a microfluidic system, according to various embodiments.

At 202, a chamber configured to receive the sample volume is provided, wherein the chamber comprises a detection region for detecting the biological entity.

At 204, a first port in fluid communication with the chamber is provided.

At 206, a second port comprising a filter in fluid communication with the chamber is provided; and wherein a fluid provided to the first port or the second port flows between the first port and the second port through the chamber.

Fabrication and Experimental Data

The fabrication of the microfluidic system of various embodiments will now be described as follows, by way of examples and not limitations.

Microfluidic System Design

FIGS. 3A to 3D show schematic views of a microfluidic system 102, according to one embodiment. The microfluidic system 102 may include a bottom silicon microchip 104 including a microelectrode array 300 for use in label-free detection and a pair of microfluidic chambers 106a, 106b, a first port 110 and a second port 112 with an integrated microfilter membrane 114. Each of the pair of microfluidic chambers 106a, 106b, may have a volume of about 4 μl. The membrane filter 114 may have a pore size of about 3 μm. The microelectrode array 300 may be formed therein or thereon the silicon microchip 104 or integrated on the silicon microchip 104 to form a microelectrode array (MEA) chip. Therefore, the detection regions of the microfluidic system 102 may be integrated on the silicon microchip 104.

Figure 3A:
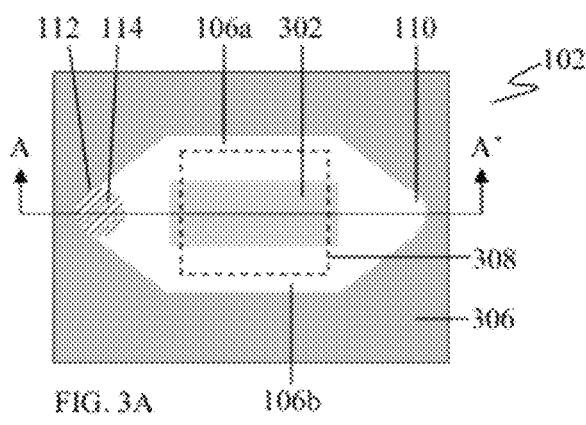
FIGS. 3A to 3D show schematic views of a microfluidic system, according to one embodiment.
Figure 3B:
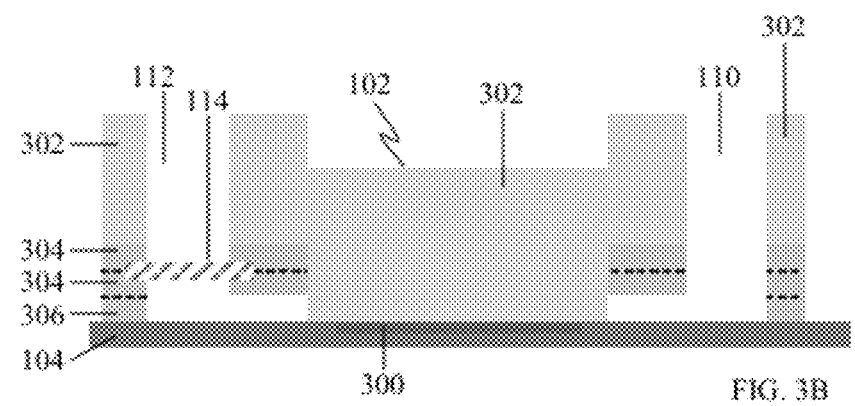

FIG. 3A shows a schematic bottom view of the microfluidic system 102, according to various embodiments, with the silicon microchip 104 including the microelectrode array 300 removed, for illustration purposes. FIG. 3B shows a schematic cross-sectional view of the microfluidic system 102, taken along the line A-A' of FIG. 3A.

As shown in FIG. 3B, the microfluidic system 102 may include a plastic chamber structure 302, two intermediate tape layers 304 and a bottom tape layer 306. Based on FIGS. 3A and 3B, the microelectrode array 300 may be provided to cover a portion of the silicon microchip 104 corresponding to the positions of the chambers 106a, 106, and the bottom surface of the plastic chamber 302, as represented by the dotted line box 308 in FIG. 3A. In various embodiments, the plastic chamber structure 302 may be attached to the microchip 104 via the two intermediate tape layers 304 and the bottom tape layer 306. In various embodiments, the two intermediate tape layers 304 and the bottom tape layer 306 may be layers of double-sided tape.

Figure 3C:
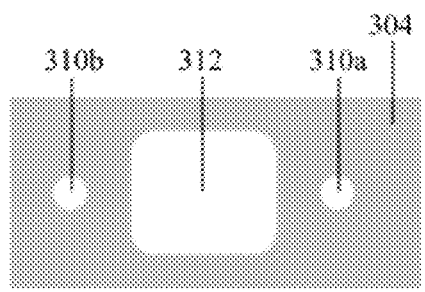
Figure 3D:
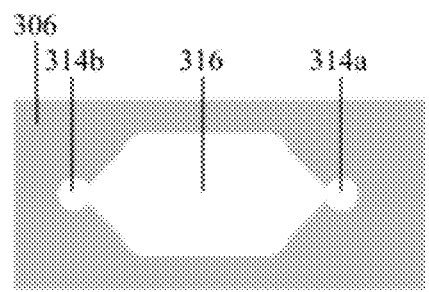

FIGS. 3C and 3D show schematic top views of the tape layers 304 and 306, respectively, according to various embodiments. The intermediate tape layer 304 includes the openings 310a, 310b, corresponding to the first port 110 and the second port 112, respectively. The intermediate tape layer 304 further includes the opening 312 such that a surface of the plastic chamber structure 302 and the chambers 106a, 106b, may contact the microelectrode array 300 and the silicon microchip 104.

In various embodiments, the bottom tape layer 306 includes the openings 314a, 314b, corresponding to the first port 110 and the second port 112, respectively. The bottom tape layer 306 further includes the opening 316 such that a surface of the plastic chamber structure 302 and the chambers 106a, 106b, may contact the microelectrode array 300 and the silicon microchip 104.

Figure 3E:
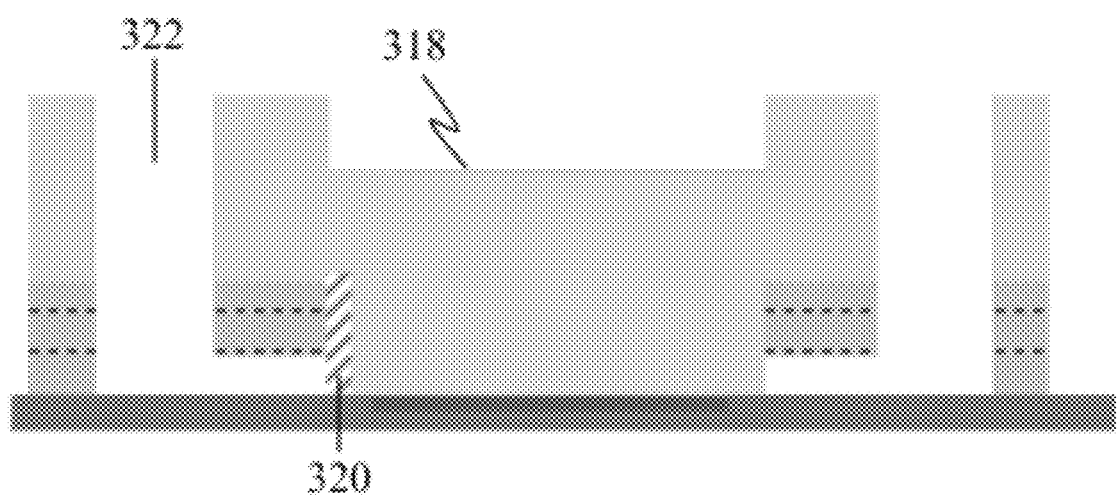
FIG. 3E shows a schematic side view of a microfluidic system, according to one embodiment.

In a further embodiment, the filter may be implemented in the vertical configuration in the second port, or in other words, arranged vertically in the second port, which may affect the flow pattern and provide certain advantages. FIG. 3E shows a schematic side view of a microfluidic system 318 with a vertically configured filter 320, according to one embodiment. The embodiment of FIG. 3E is similar to the embodiment of FIG. 3B, including the elements or parts of the microfluidic system, except for the configuration of the filter. In the embodiment of FIG. 3B, the filter 114 is implemented in the horizontal configuration in the second port 112. In the embodiment of FIG. 3E, the filter 320 is implemented in the vertical configuration in the second port 322. Therefore, the filter 320 is configured parallelly to the wall of the second port 322. Such a configuration may be relatively less prone to blockage as a result of sedimentation on the filter 320. It should be appreciated that the microfluidic system 318 with the vertically configured filter 320 may be implemented in any design suitable for applications.

In various embodiments, it should be appreciated that any number of the intermediate tape layer 304 and the bottom tape layer 306 may be provided.

Surface chemistry, as known in the art, may be performed to attach a linker, such as a thiol linker, to the microelectrode array 300. The microfluidic system 102 including the plastic chamber structure 302 may then be mounted on the silicon microchip 104. Capture molecules for specific cell capture, such as antibodies, may be attached via a EDAC/NHS (1-(3-Dimethylaminopropyl)-3-ethylcarbodiimide hydrochloride/N-hydroxy succinimide) coupling to the linker. The surface of the silicon microchip 104 not covered by the microelectrode array 300 may be passivated with a repellent material, for example polyethylene glycol (PEG). Therefore, there may be a layer of coating including linkers, capture molecules and the repellent material. Subsequently, the microfluidic system 102 mounted on the silicon microchip 104 may be stored in a refrigerator to preserve or maintain the functionalities of the coated layer. A buffer solution may be provided in the microfluidic system 102 to protect the coated layer. In alternative embodiments, other storage methods as known in the art may be used, for example dried, frozen or vacuum storage.

The use of a repellent material on the device surface not covered by microelectrode array 300 reduces non-specific adhesion of biological entities and increases specific detection of the target biological entity, which may be helpful when the number of the target biological entity is relatively small.

Figure 4:
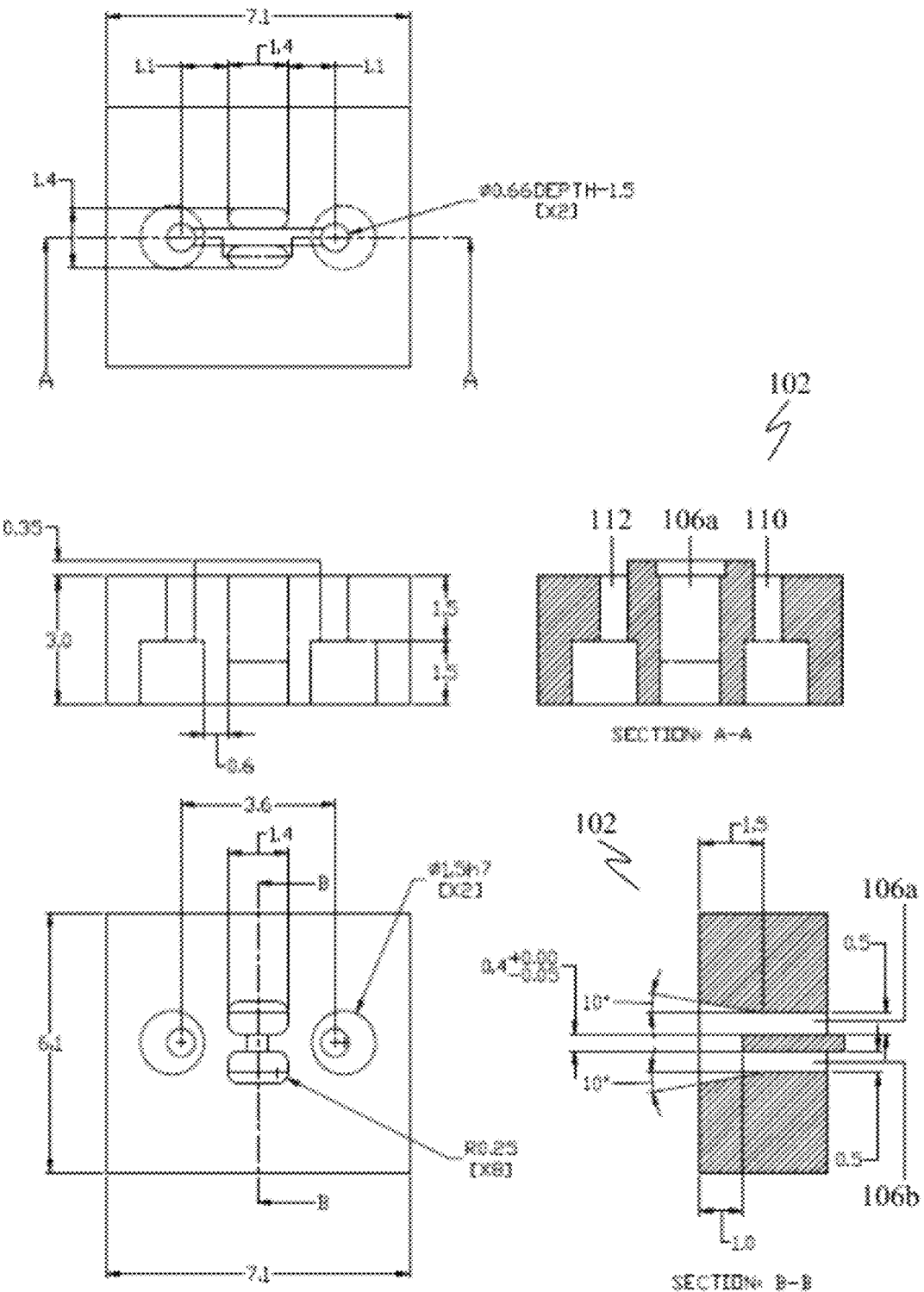
FIG. 4 shows technical drawings of the microfluidic system according one embodiment. The dimension in FIG. 4 is in millimeter (mm).

FIG. 4 shows the technical drawings of the plastic chamber structure 302 according to one embodiment. FIG. 4 shows the plastic chamber structure 302 in top, bottom and cross-sectional views and the dimensions of the plastic chamber structure 302 in millimeter (mm).

Figure 5A:
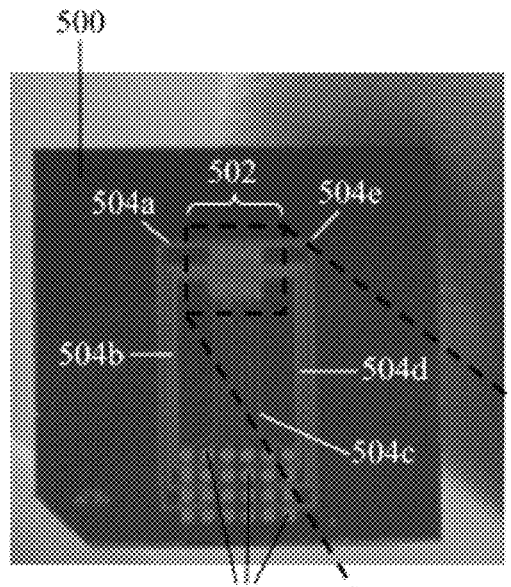
FIG. 5A shows a top view of a microchip, according to one embodiment.

FIG. 5A shows a top view of a microchip 500, according to one embodiment, that may be provided with the microfluidic system of various embodiments. The microchip 500 may include a microelectrode array 502 and a plurality of electrical interconnections, for example 504a, 504b, 504c, 504d, 504e, for connection to a plurality of contact pads 506. The plurality of contact pads 506 may be connected to a printed circuit board (PCB) for electrical control of the microelectrode array 502 and processing. The microchip 500 may be a silicon microchip. The use of the PCB-based signal processing may reduce the processing and detection time of the biological entity to below 1 hour, which may allow the use of the microfluidic system of various embodiments in a point-of-care (POC) setting for diagnosis and monitoring of acute and chronic diseases, such as heart attacks and atherosclerosis progression.

Figure 5B:
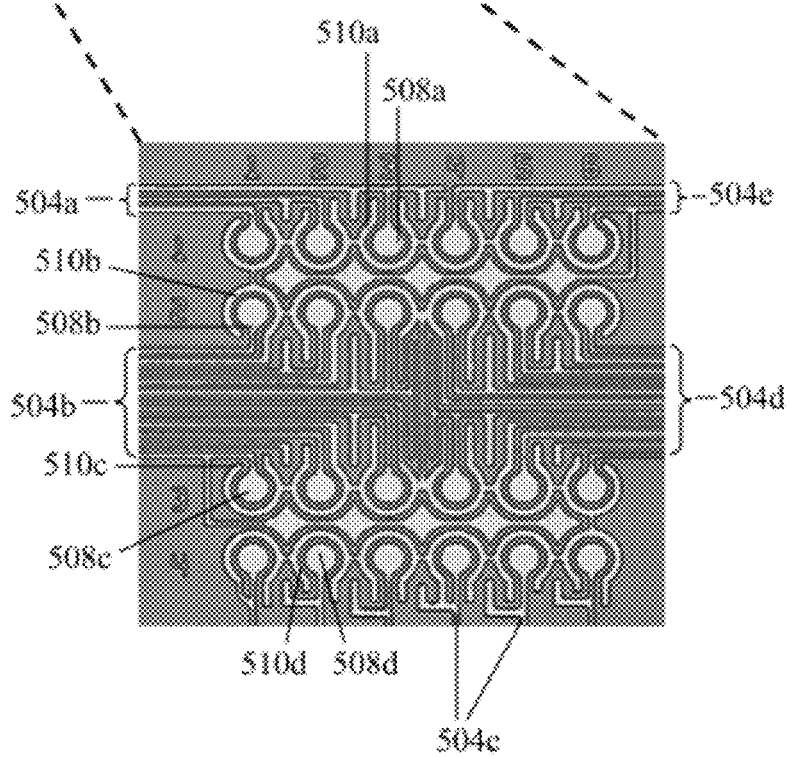
FIG. 5B shows a top view of a microelectrode array according to one embodiment, provided on the microchip of the embodiment of FIG. 5A.

FIG. 5B shows a top view of the microelectrode array 502 according to one embodiment, provided on the microchip 500 of the embodiment of FIG. 5A. As shown in FIG. 5B, the microelectrode array 502 includes 24 pairs of electrodes, arranged in a 4×6 array. In various embodiments, the number of the plurality of contact pads 506 may correspond to the number of the pairs of electrodes.

In various embodiments, each pair of electrodes may be identified by its row number, as indicated on the left side of FIG. 5B and its column number, as indicated on the top of FIG. 5B. Each of the 24 pairs of electrodes may include an inner electrode, for example 508a, 508b, 508c, 508d, and an outer electrode, for example 510a, 510b, 510c, 510d. In various embodiments, the inner electrodes, for example 508a, 508b, 508c, 508d, may be working electrodes and in the shape of a disc, while the outer electrodes, for example 510a, 510b, 510c, 510d, may be reference electrodes and in the shape of a horseshoe that substantially surround the inner electrodes, for example 508a, 508b, 508c, 508d. The outer electrodes, for example 510a, 510b, 510c, 510d, may be shorted together or in electrical communication with each other to function together as a collective electrode, to provide a relatively bigger surface area to increase sensitivity, while the inner electrodes, for example 508a, 508b, 508c, 508d, may be controlled individually for relatively high sensitive impedance measurements or shorted together or in electrical communication with each other to function together as a collective electrode, to generate a spatially non-uniform electric filed that induces dielectrophoresis (DEP), thereby resulting a dielectrophoretic force.

Figure 6A:
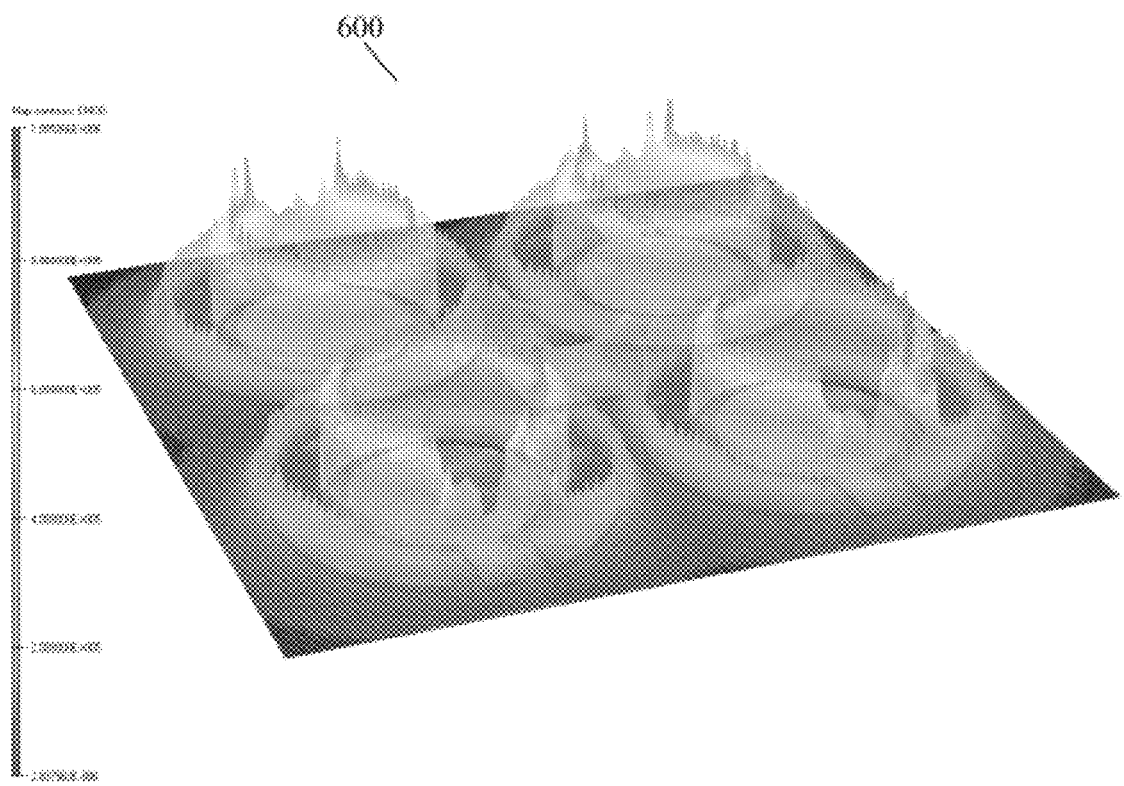
FIG. 6A shows a simulation plot of the non-uniform electric fields generated by a microelectrode array, according to various embodiments.

FIG. 6A shows a simulation plot 600 of the non-uniform electric fields, giving rise to a dielectrophoretic field, generated by a microelectrode array, according to various embodiments. As shown in FIG. 6A, the electric field generated has electric field minima occurring at the centres of the inner electrodes, which when used for negative dielectrophoresis (DEP), may direct and concentrate the target cells at the centres of the inner electrodes for impedance measurement.

Figure 6B:
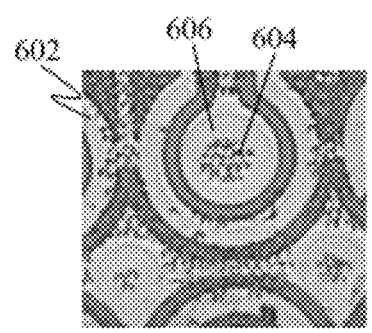
FIG. 6B shows an optical microscopy image of a microelectrode array with cells, according to various embodiments.

FIG. 6B shows an optical microscopy image of a microelectrode array 602 with cells, with an applied electrical signal having a peak-to-peak amplitude of about 1.5 V and a frequency of 1 MHz. FIG. 6B shows a plurality of cells 604 concentrated in the centre of the inner electrode 606 of the microelectrode array 602, as a result of negative DEP.

Referring to FIG. 5, in various embodiments, the inner electrodes of the first row of the pairs of electrodes may be connected to the plurality of contact pads 506 via the interconnections 504a, 504e. The inner electrodes of the second and third rows of the pairs of electrodes may be connected to the plurality of contact pads 506 via the interconnections 504b, 504d. The inner electrodes of the fourth row of the pairs of electrodes may be connected to the plurality of contact pads 506 via the interconnections 504c. The outer electrodes, which are shorted and in electrical communication with each other may be connected to the plurality of contact pads 506 via the interconnections 504b, 504d.

In various embodiments, surface chemistry, may be performed to functionalise the inner electrodes, for example 508a, 508b, 508c, 508d, and the outer electrodes, for example 510a, 510b, 510c, 510d, of the microelectrode array 502, with a linker, such as a thiol linker. Capture molecules for specific cell capture, such as antibodies, may then be attached via a EDAC/NHS (1-(3-Dimethylaminopropyl)-3-ethylcarbodiimide hydrochloride/N-hydroxy succinimide) coupling to the linker. The surface of the silicon microchip 104, which may be silicon oxide, not covered by the microelectrode array 300 may be passivated with a cell repellent material, for example polyethylene glycol (PEG).

Various embodiments will now be described by the following illustrative non-limiting examples.

Jurkat Cell Filtering

In order to assist in the development and testing of the microfluidic system of various embodiments, a sample solution of cultured cells, such as the Jurkat cells of T-lymphocytes, having the same concentration as PBMCs in blood (ie. about $6 \times 10^6$ cells/ml) and in a volume sufficient to saturate the detection region, for example about 12000 cells in about 2 µl, was used.

Figure 7A:
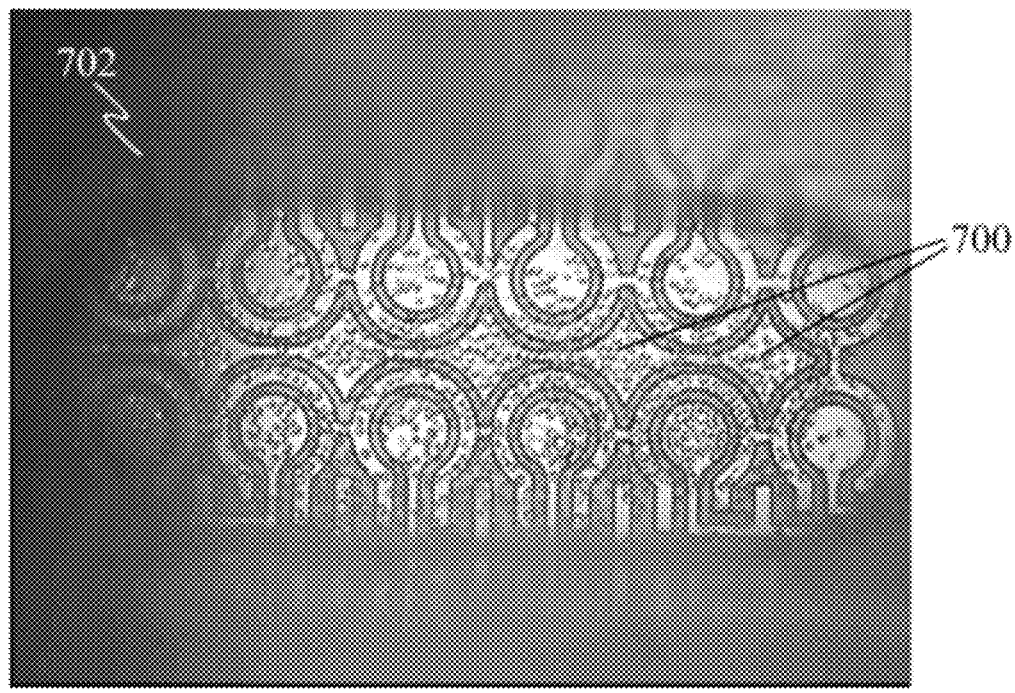
FIGS. 7A to 7C show optical microscopy images of microelectrode arrays with cells, according to various embodiments.
Figure 7B:
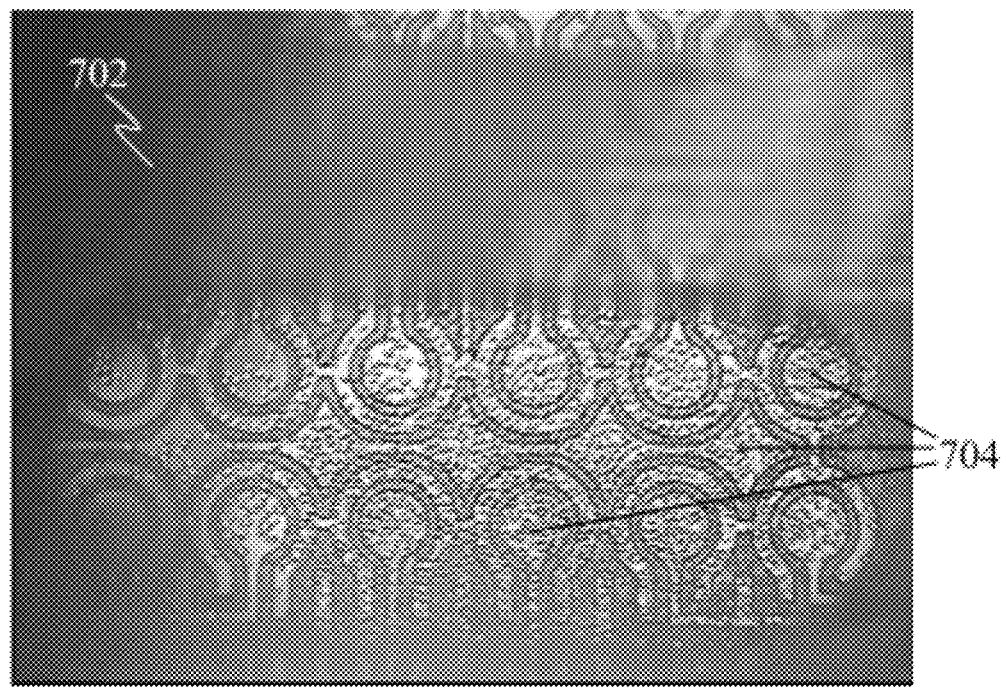
Figure 7C:
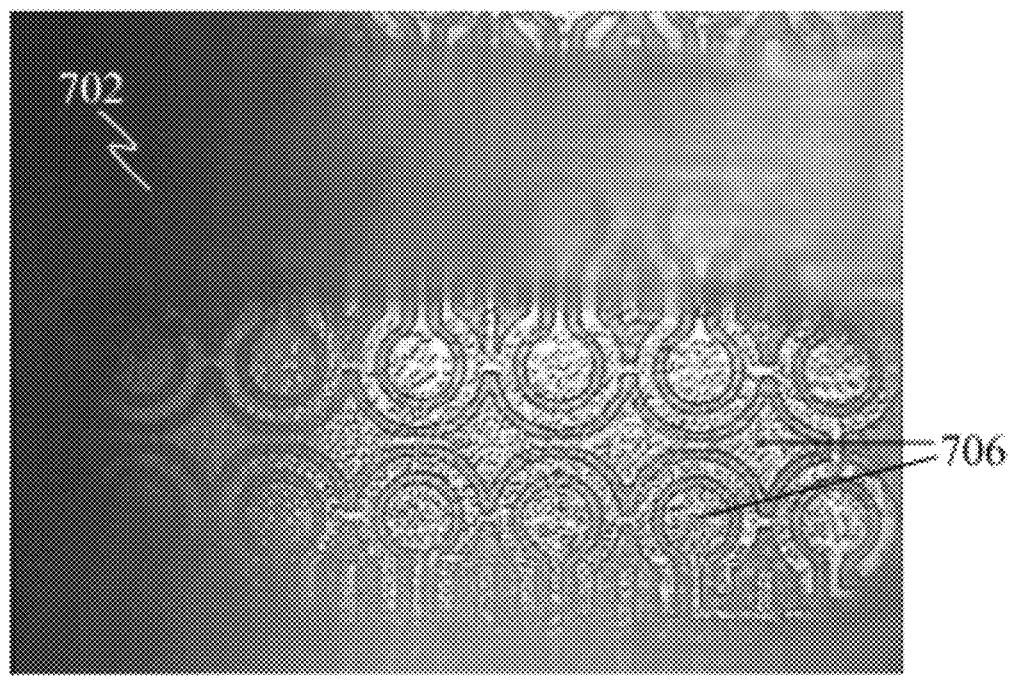

The cells were provided to the microfluidic system of various embodiments using the procedures of various embodiments as previously described, and filtered at different flow rates and back-flushed or back-flow at different flow rates. The cells were then incubated with DEP to establish surface coverage of the microelectrode array. FIGS. 7A to 7C show optical microscopy images of microelectrode arrays with cells, according to various embodiments. The optical microscopy images were obtained using an Olympus BX51 Upright High Power Microscope.

FIG. 7A shows an optical microscopy image of cells 700 on the surface of the microelectrode array 702 after filtration at a flow rate (ie. the filtering flow rate) of about 400 µl/min and incubation with DEP for about 5 minutes. FIG. 7B shows an optical microscopy image of cells 704 on the surface of the microelectrode array 702 after a subsequent backflow at a flow rate (ie. the backflow rate) of about 800 µl/min and incubation with DEP for about 5 minutes. FIG. 7C shows an optical microscopy image of cells 706 on the surface of the microelectrode array 702 after backflow at a flow rate of about 800 µl/min and incubation with DEP for about 16 minutes.

As can be seen from FIG. 7A, cells 700 are present on the surface of the microelectrode array 702 after the filtration process, which means that not all the cells flow towards the membrane filter and pass through the membrane filter and therefore, may be sedimented during incubation with DEP. In various embodiments, a multiple number of the filtration process may be carried out to flow the sample, which may be a blood sample, towards the membrane filter.

Figure 7D:
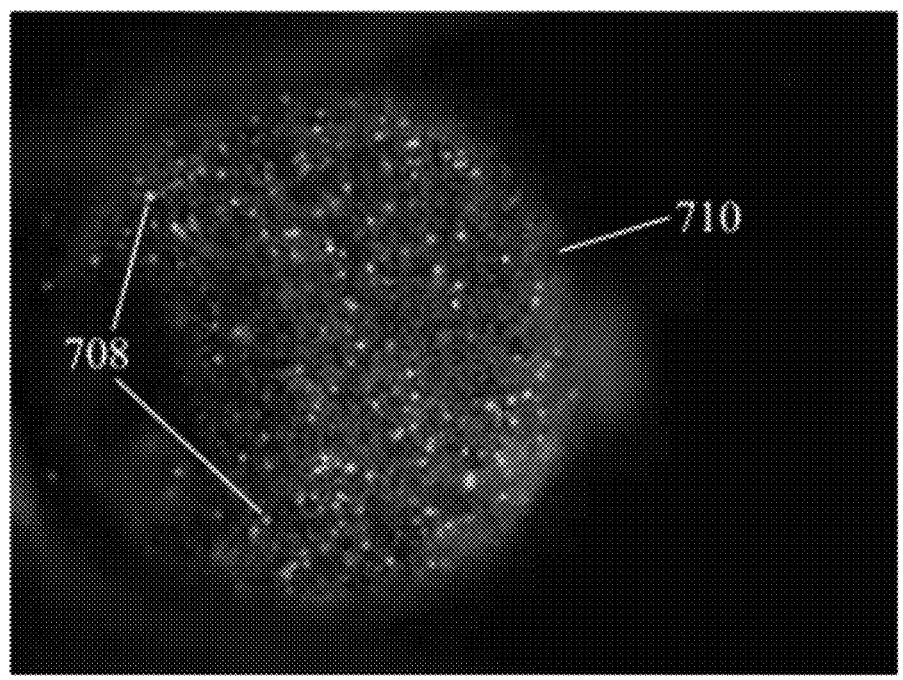
FIGS. 7D and 7E show fluorescence microscopy images of cells at a membrane filter and in waste, respectively, according to various embodiments.
Figure 7E:
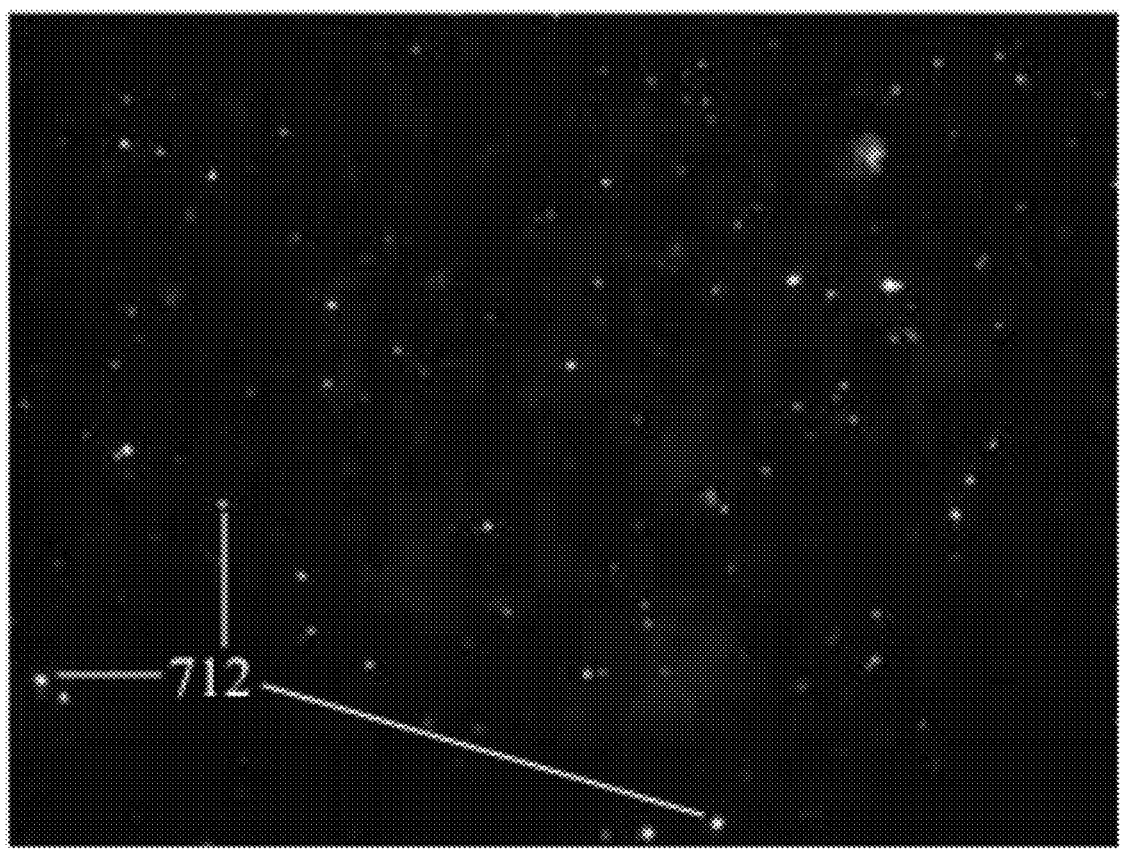

In addition, the backflow efficiency was ascertained by also staining the cells on the filter membrane using a fluorescent dye (for example Calcein AM by Invitrogen) that stains living cells and produces green fluorescence. FIGS. 7D and 7E show fluorescence microscopy images of cells 708 retained at a membrane filter 710 and cells 712 in waste after filtration, respectively, according to various embodiments. The fluorescence microscopy images were obtained using an Olympus BX61 Upright Fluorescent Microscope with an FITC (fluorescein isothiocyanate) filter. The cells 708 retained at the membrane filter was estimated to amount to about 201 cells.

It should be appreciated that other conventional methods may also be carried out to establish the number of dead cells and cells that have passed through the filter.

The number of cells retained on the membrane filter, being about 200 cells, is relatively large and may affect the detection of rare cells, which may be present in a relatively small number, for example 10 cells or less. In addition, as shown in FIGS. 7B and 7C, the cells 704, 706, after backflow, may be affected by the backflow rate and may be incubated on one side of the microelectrode array 702, rather than incubated substantially uniformly over the surface of the microelectrode array 702.

Figure 8A:
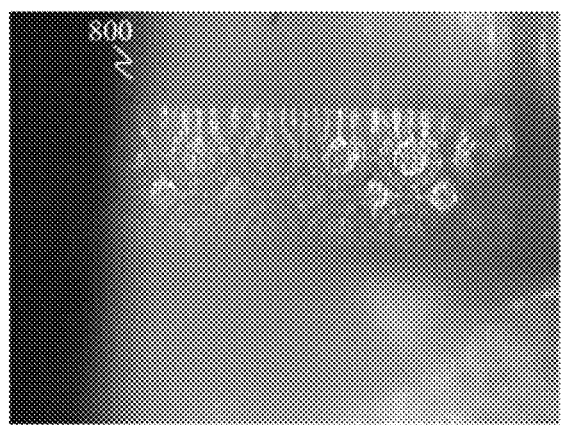
FIGS. 8A to 8C show optical microscopy images of microelectrode arrays with cells, according to various embodiments.
Figure 8B:
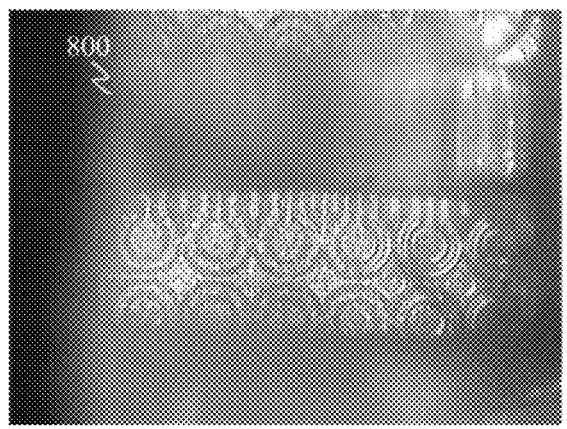
Figure 8C:
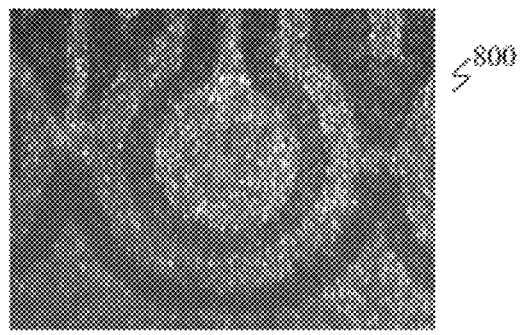

FIG. 8A shows an optical microscopy image of cells on the surface of the microelectrode array 800 after filtration at a flow rate of about 200 µl/min, without DEP incubation. FIG. 8B shows an optical microscopy image of cells on the surface of the microelectrode array 800 after a subsequent backflow at a flow rate of about 600 µl/min and incubation with DEP for about 10 minutes. FIG. 8C shows a close-up sectional view of FIG. 8B, indicating a relatively large number of cells present on the microelectrode array 800, which may affect the detection efficiency of specific cells for the microfluidic system of various embodiments.

Therefore, in various embodiments, the filtering flow rate and the backflow rate may need to be provided so that a substantially optimum level of cell numbers may be provided on the microelectrode arrays for detection.

Figure 9:
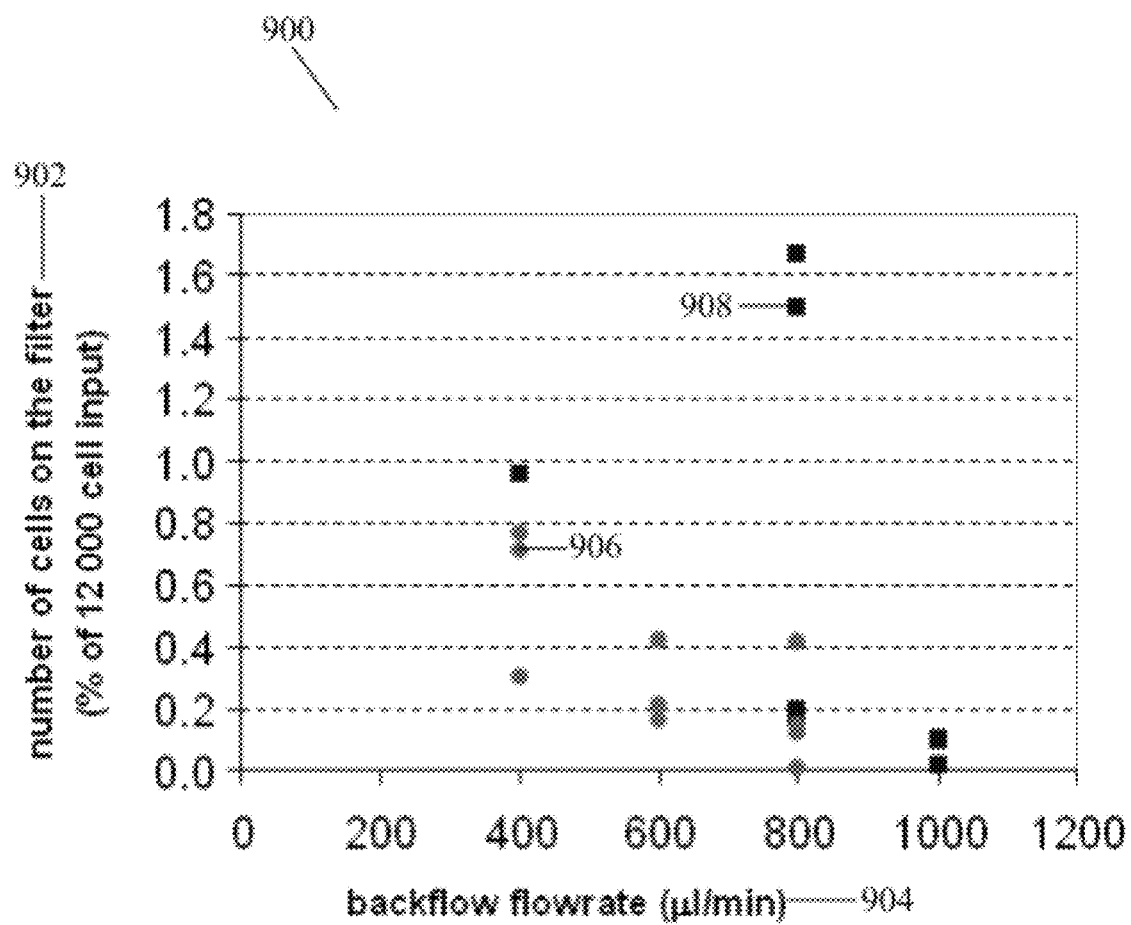
FIG. 9 shows a plot of sample filtration efficiency, according to various embodiments.

FIG. 9 shows a plot 900 of sample preparation efficiency, according to various embodiments. The plot 900 was obtained based on the preparation and filtration of PBMCs from a blood sample, and is shown in terms of the number of cells on the filter (as a percentage of input with 12000 cells) 902 against the backflow rate 904. The number of cells on the filter refers to the number of cells remaining on the filter, after filtration and backflow processing, in accordance with various embodiments.

The round data points, as represented by 906, were obtained for filtration processes at a flow rate of about 200 µl/min, while the square data points, as represented by 908, were obtained for filtration processes at a flow rate of about 400 µl/min.

Figure 10A:
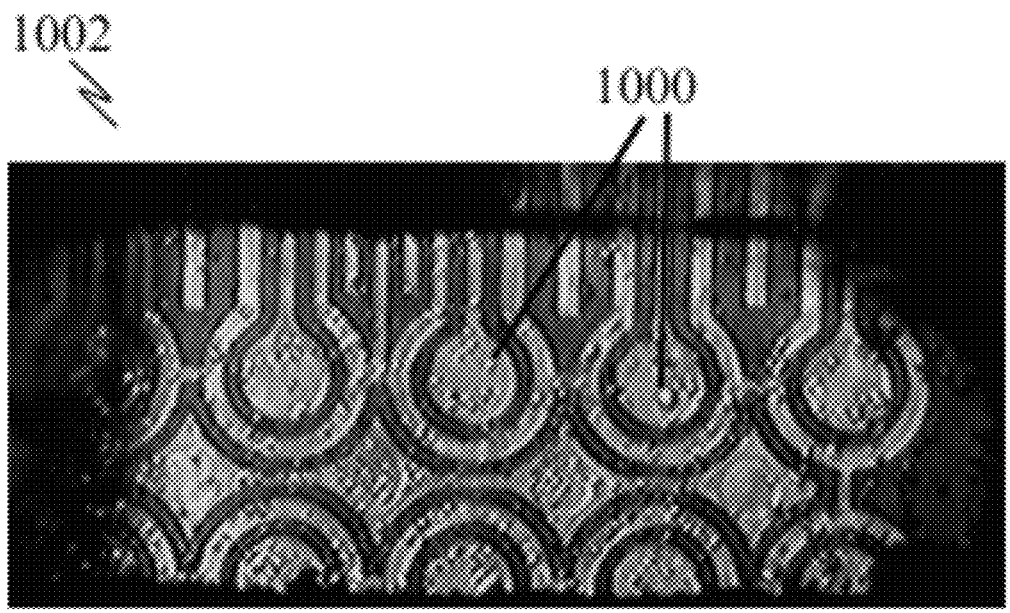
FIGS. 10A and 10B show optical microscopy images of microelectrode arrays with cells, according to various embodiments.
Figure 10B:
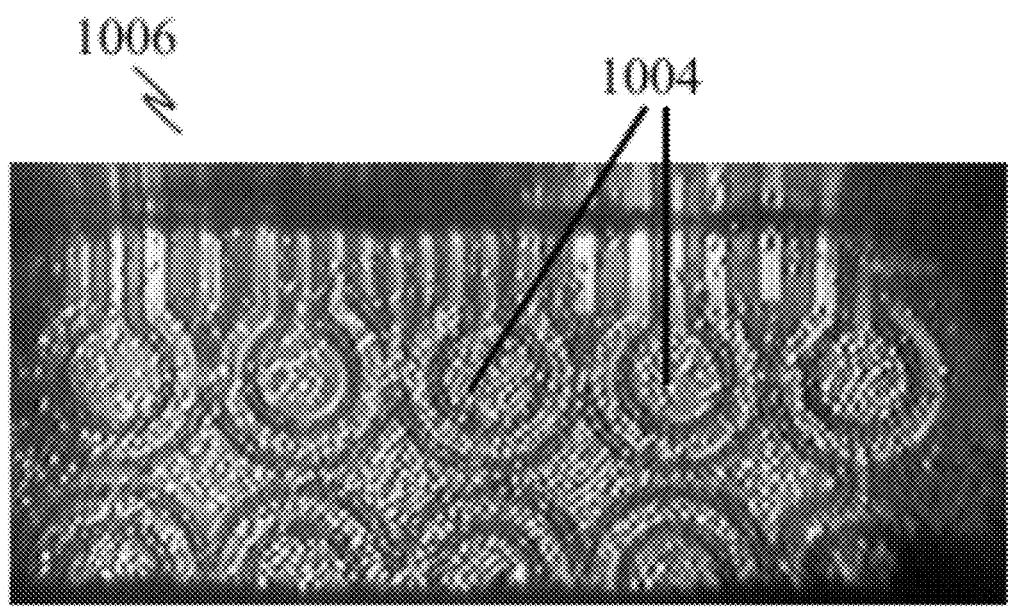

FIG. 10A shows an optical microscopy image of PBMCs 1000 on the surface of the microelectrode array 1002 after filtration at a flow rate of about 200 µl/min and incubation with DEP for about 5 minutes. FIG. 10B shows an optical microscopy image of PBMCs 1004 on the surface of the microelectrode array 1006 after backflow at a flow rate of about 600 µl/min and incubation with DEP for about 10 minutes.

As shown in FIG. 10B, the cells 1004, after backflow, was incubated substantially uniformly over the surface of the microelectrode array 1006.

Spiked Blood Preparation

About 750 CD34 cells (or endothelial progenitor cells, EPCs) were spiked in about 1 µl of blood and were provided to the microfluidic system of various embodiments and processed according to the procedures of various embodiments as previously described. In addition, a pure blood sample was also prepared and processed according to the procedures of various embodiments as previously described. The CD34+ cells were specifically captured on the microelectrode array using negative dielectrophoresis (DEP), specific antibody recognition and also microfluidics to wash away the non-specific cells.

Figure 11A:
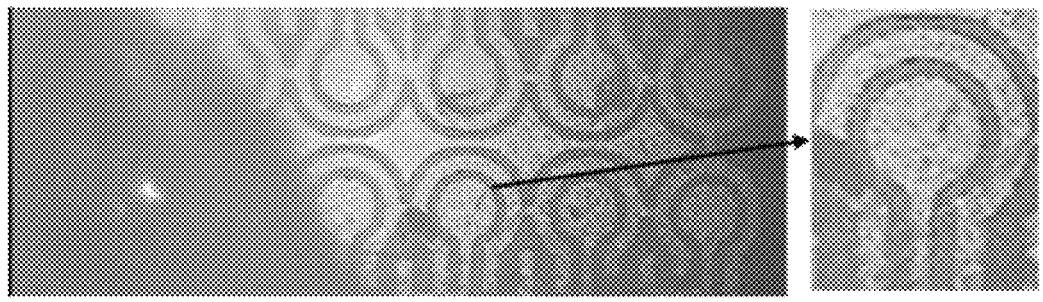
FIGS. 11A and 11B show optical microscopy images of a microelectrode array with cells from a sample of pure blood, according to various embodiments.
Figure 11B:
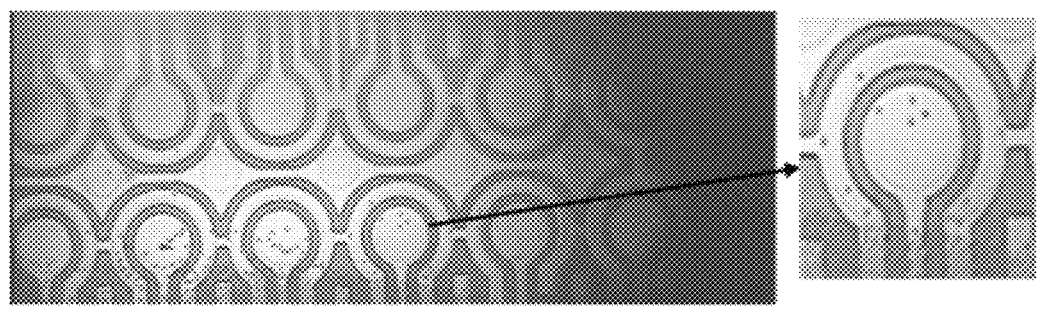

FIG. 11A shows an optical microscopy image of a microelectrode array with PBMCs from the sample of pure blood, after purification of the PBMCs involving filtration at a flow rate of about 50 µl/min for about 2 minutes, and backflow, performed twice, at a flow rate of about 600 µl/min (twice) that transferred the PBMCs into the open chambers, while FIG. 11B shows an optical microscopy image of the same microelectrode array of FIG. 11A, after a further washing process carried out at a flow rate of about 50 µl/min for about 2 minutes.

Figure 11C:
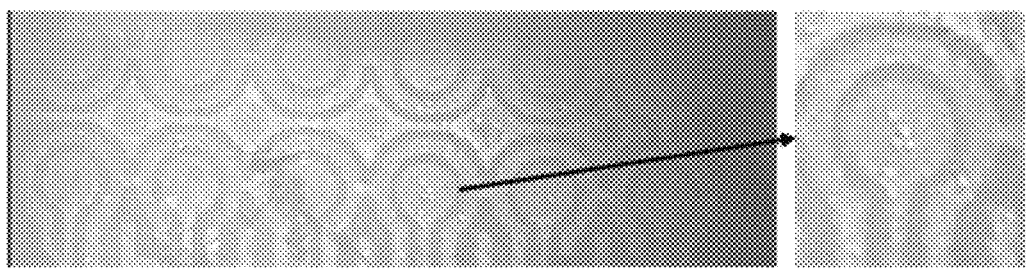
FIGS. 11C and 11D show optical microscopy images of a microelectrode array with cells from a sample of spiked blood, according to various embodiments.
Figure 11D:
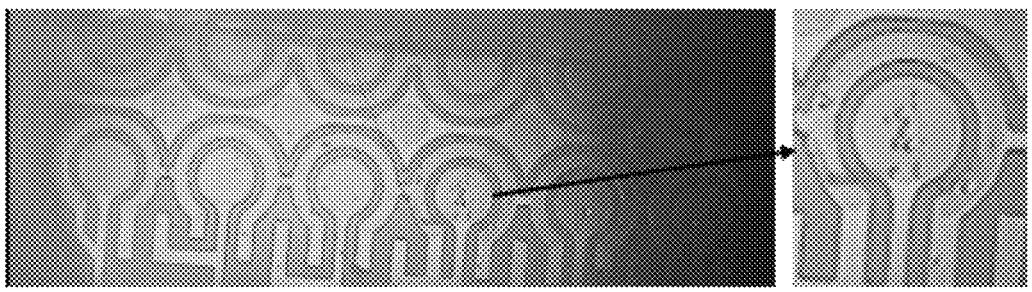

FIG. 11C shows an optical microscopy image of a microelectrode array with cells from the sample of spiked blood, after filtration at a flow rate of about 50 µl/min for about 2 minutes, and backflow, performed twice, at a flow rate of about 600 µl/min (twice) that transferred the cells into the open chambers, while FIG. 11D shows an optical microscopy image of the same microelectrode array of FIG. 11C after a further washing process carried out at a flow rate of about 50 μl/min for about 2 minutes.

While a relatively large number of cells were present after the backflow processes (FIGS. 11A and 11C), after the washing process, most of the cells were removed, leaving the CD34+ cells on the surfaces of the microelectrode arrays.

In addition, separate samples of CD34− cells and CD34+ cells spiked in about 1 μl of blood were provided to the microfluidic system of various embodiments and processed according to the procedures of various embodiments as previously described. Cell capture was carried out using negative DEP and specific capture molecules for CD34+ cells.

Figure 12A:
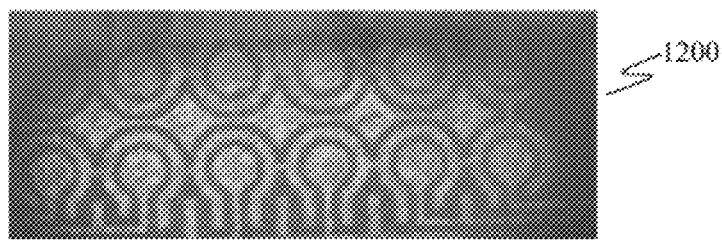
FIGS. 12A and 12B show optical microscopy images of a microelectrode array with CD34− cells, according to various embodiments.
Figure 12B:
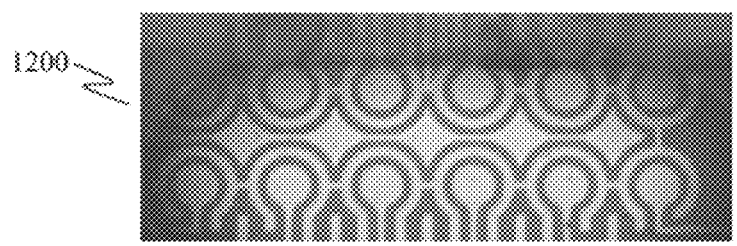
Figure 12C:
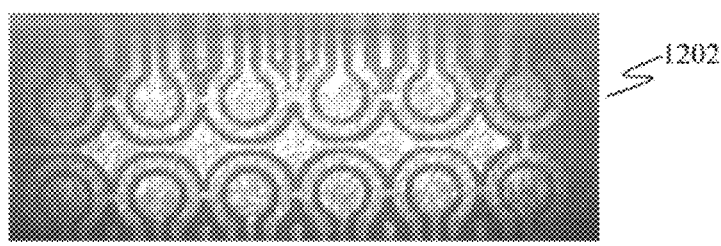
FIGS. 12C and 12D show optical microscopy images of a microelectrode array with CD34+ cells, according to various embodiments.
Figure 12D:
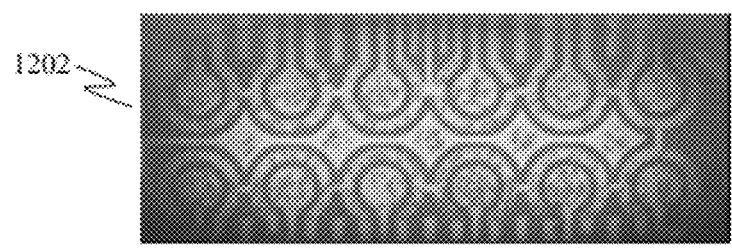

FIGS. 12A and 12B show the optical microscopy images of the microelectrode array 1200 with a sample containing CD34− cells, before and after a washing process carried out at a flow rate of about 400 μl/min for about 2 minutes. FIGS. 12C and 12D show the optical microscopy images of the microelectrode array 1202 with a sample containing CD34+ cells, before and after a washing process carried out at a flow rate of about 400 μl/min for about 2 minutes.

As shown in FIGS. 12A and 12C before the washing process, a relatively large number of cells were present on the microelectrode arrays 1200, 1202. After the washing process, most of the cells including the CD34− cells were washed away from the microelectrode array 1200, as shown in FIG. 12B, while the CD34+ cells remained on the microelectrode array 1202, as shown in FIG. 12D, due to the specific capture of CD34+ cells by the capture molecules on the microelectrode arrays 1200, 1202.

Spiked Blood, with Integrated Impedance Detection

Using the procedure of various embodiments as described above for the preparation and processing of spiked blood sample, impedance measurement or impedance spectroscopy was carried out for the detection of the cells captured on the microelectrode array. The cells were detected by impedance spectroscopy in a batch operation mode, which was able to detect cells at relatively small numbers (<1000 cells), with relatively better sensitivity than the clinically-significant cut-off of about 0.5% EPCs in blood (Hill J. M., "Circulating Endothelial Progenitor Cells, Vascular Function, and Cardiovascular Risk", N. Engl. J. Med., 2003, 348(7), 593).

Figure 13A:
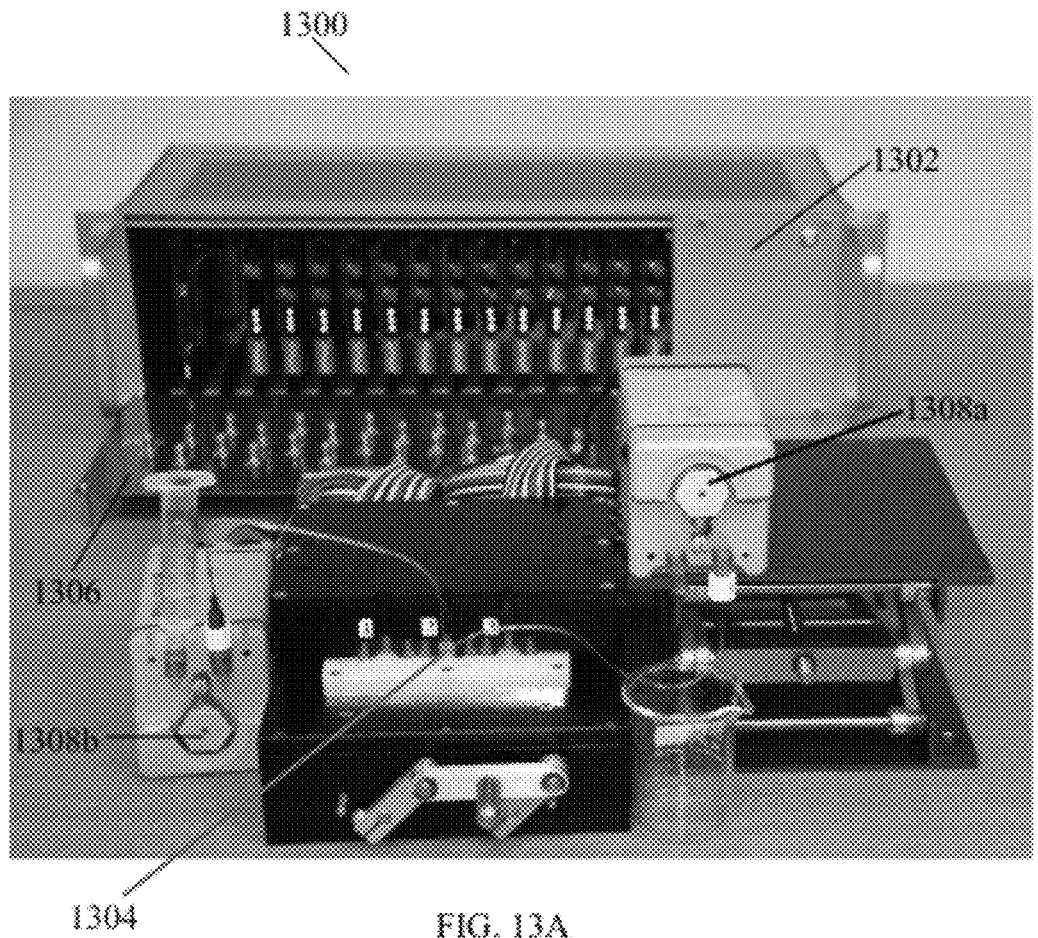
FIG. 13A shows a system for measuring impedance, according to various embodiments.

FIG. 13A shows a system 1300 for measuring impedance, according to various embodiments. The system 1300 may be an integrated PCB-based electronic system for the simultaneous detection and measurements of impedance based on 24 pairs of electrodes of the microelectrode array of the microfluidic system 1304. The system 1300 includes a PCB-based measurement system 1302 including 24 channels corresponding to the 24 pairs of electrodes. The PCB-based measurement system 1302 may be connected to a computer and controlled using, for example a software such as Labview.

The system 1300 further includes a custom field-programmable gate array (FPGA) board 1306 connected to the measurement system 1302 and to the microelectrode array (not shown). The system 1300 further includes the pumps 1308a, 1308b, coupled respectively to the first and second ports of the microfluidic system 1304. The pumps 1308a, 1308b, are used to supply a buffer solution to the microfluidic system 1304 and to move the buffer solution along the fluidic microchannels and the chamber of the microfluidic system 1304.

Figure 13B:
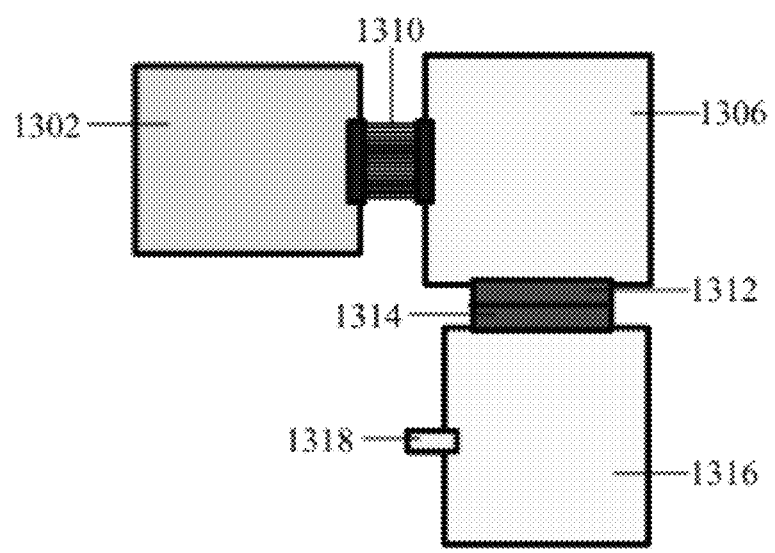
FIG. 13B shows a schematic diagram illustrating the PCB-based interconnections of the embodiment of FIG. 13A.

FIG. 13B shows a schematic diagram illustrating the PCB-based interconnections of the embodiment of FIG. 13A. The PCB-based measurement system 1302 is connected to the (FPGA) board 1306 via the electrical interconnections 1310. The (FPGA) board 1306 may include a connector 1312 which is adapted to mate with the connector 1314 of a PCB card (daughter card) 1316. The PCB card 1316 further includes the connector 1318 for connection to the microelectrode array of the microfluidic system 1304 (FIG. 13A).

For detection of the target biological entities or cells (for example CD34 cells), impedance measurement was initially recorded in the presence of the buffer solution but in the absence of biological entities or cells to measure the background signal. Subsequently, after the filtration, backflow and washing processes according to various embodiments, most of the biological entities in the samples were removed, leaving the target cells on the surfaces of the microelectrode arrays. Impedance measurement was then recorded and changes in the impedance were summed up over all the electrodes of the microelectrode array.

Figure 13C:
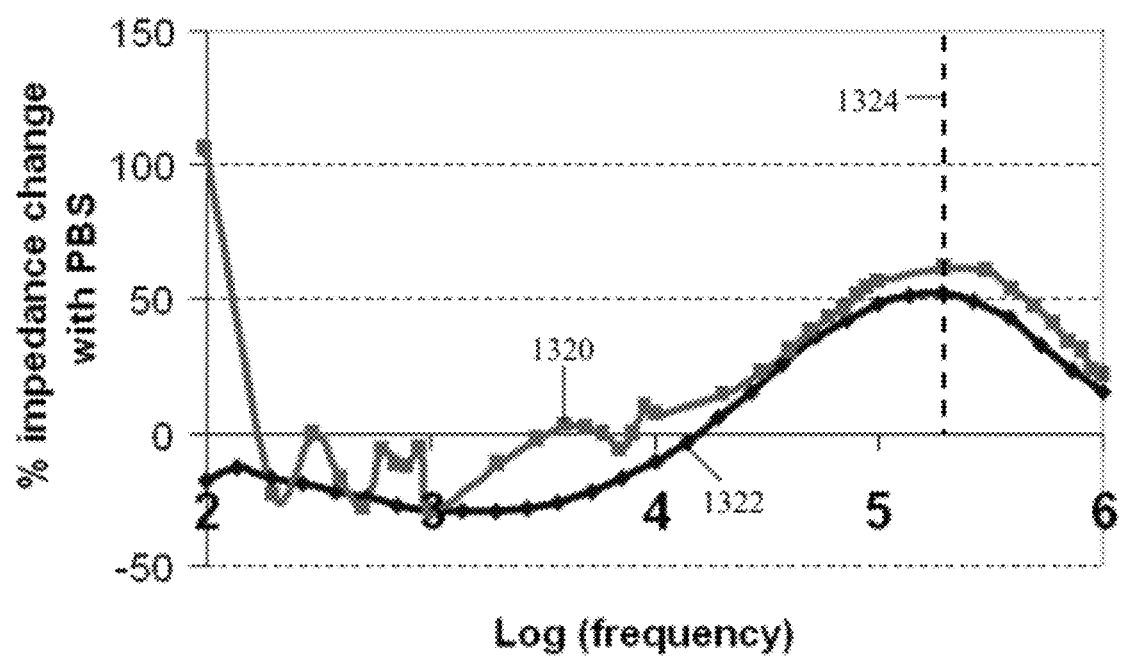
FIG. 13C shows a plot of impedance measurement based on a channel of the system of the embodiment of FIG. 13A.

FIG. 13C shows a plot 1320 of impedance measurement with a PBS solution containing cells for a channel of the system of the embodiment of FIG. 13A. For comparison purposes, a plot 1322 of impedance measurement based on a conventional set-up system is also shown. The plots 1320, 1322, show relatively good correlation for the different systems for the channel. The dotted line represented as 1324 indicates the frequency at which the impedance change or sensitivity is the highest.

Figure 14:
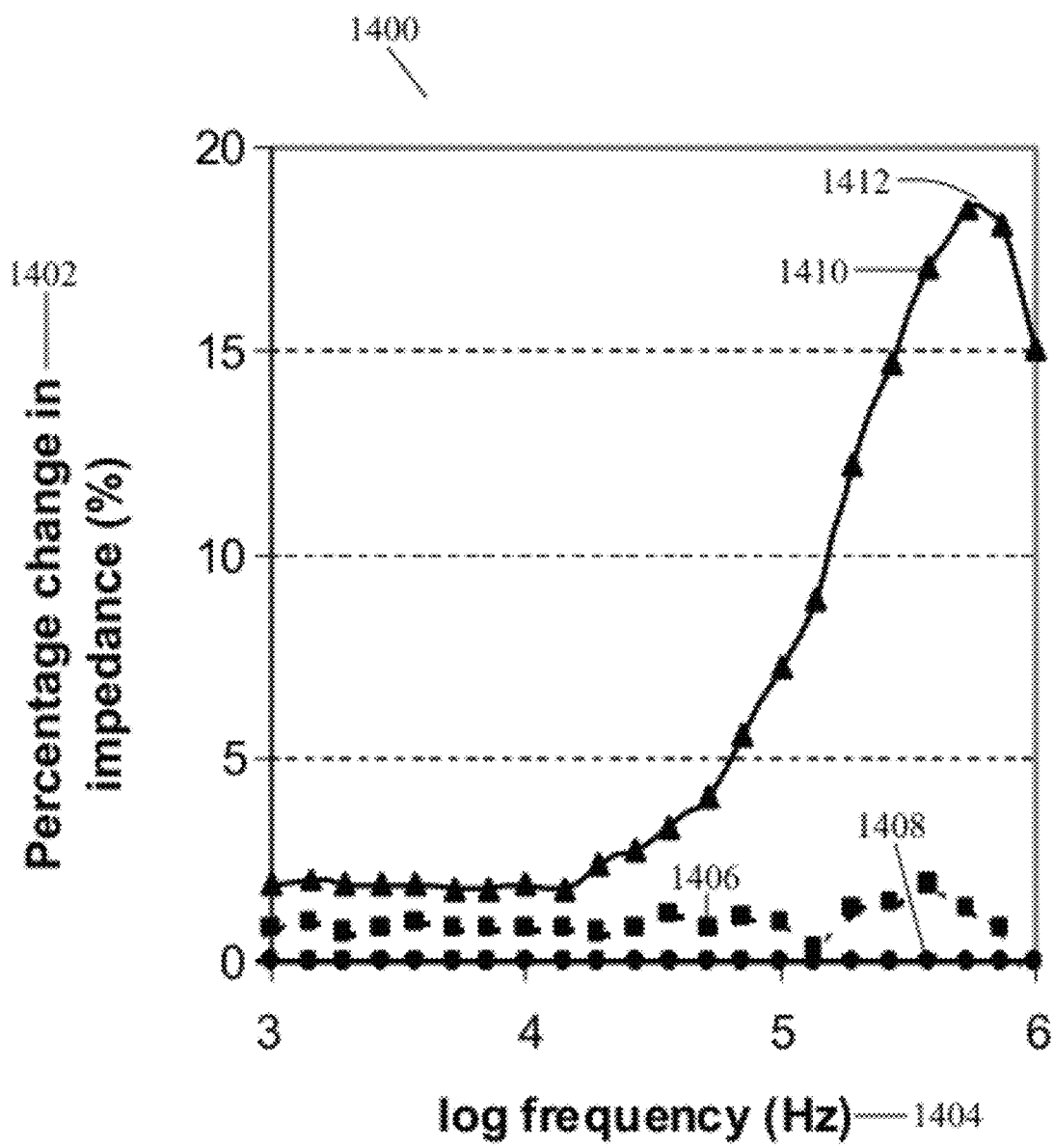
FIG. 14 shows a plot of impedance measurement, according to various embodiments.

FIG. 14 shows a plot 1400 of impedance measurement for a number of samples, according to various embodiments. The plot 1400 is shown in terms of the percentage change in impedance 1402 against frequency (in logarithm scale) 1404.

FIG. 14 shows the results for a phosphate buffered saline (PBS) buffer solution without cells, as represented by the square data points 1406, after a pre-wash with PBS without cells, as represented by the round data points 1408, and a sample with cells after a washing protocol in accordance with various embodiments, as represented by the triangular data points 1410. The percentage change in impedance 1402 observed for the data points 1406 and 1408 were low because only PBS was present, with no cell added, and these were used as background measurements.

FIG. 14 shows that the specific attachment of cells on the electrodes resulted in an increase in the real part of impedance, with a peak 1412 at around 380 kHz (corresponding to the value of approximately 5.58 in terms of the frequency in logarithm scale). The frequency for the peak 1412 indicates the frequency at which the highest sensitivity is observed for these cells and therefore serves as the basis for the frequency that should be used to detect these cells during measurements.

Figure 15:
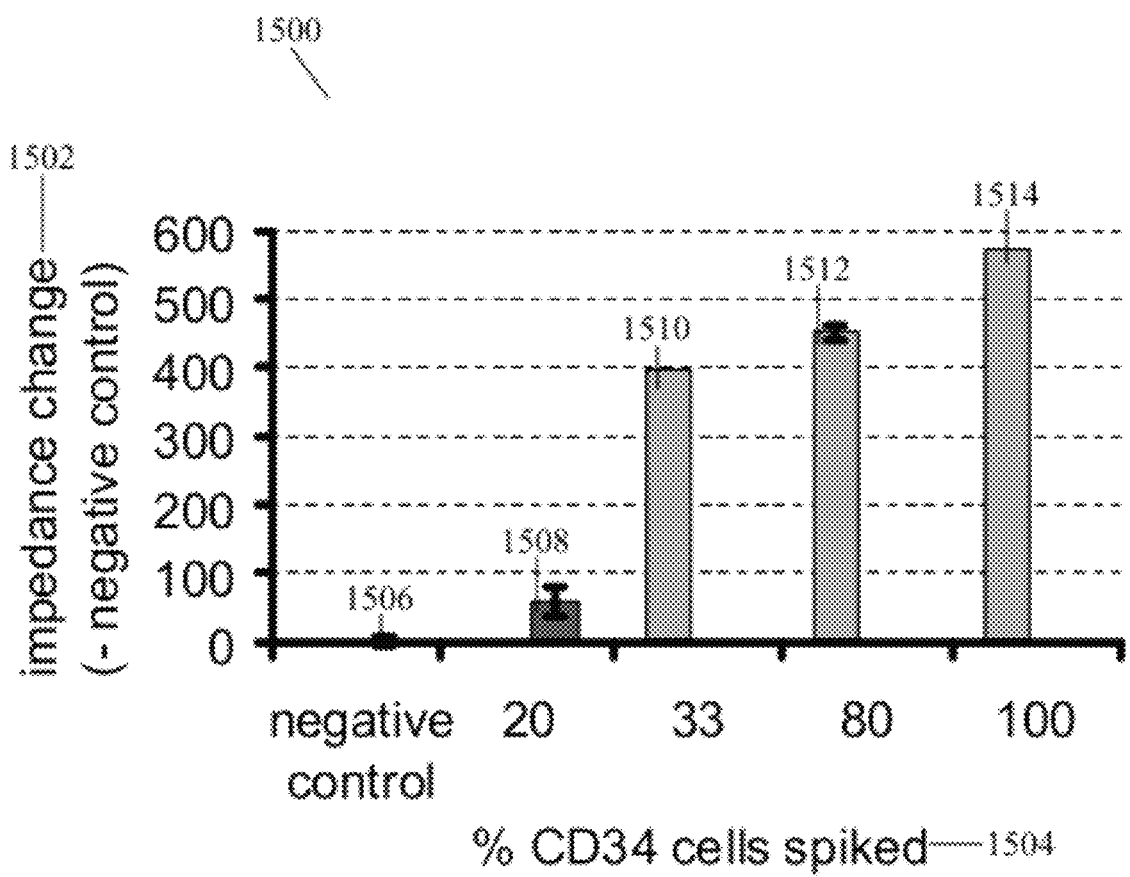
FIG. 15 shows a plot of impedance measurement for a number of samples, according to various embodiments.

FIG. 15 shows a plot 1500 of impedance measurement for a number of samples, according to various embodiments. The plot 1500 was obtained after PBMC purification and specific CD34 cell capture, and is shown in terms of the impedance change 1502 against the percentage of CD34 cells spiked in the sample 1504. The plot 1500 was obtained based on impedance measurement or spectroscopy carried out at the frequency of approximately 380 kHz. The detection time for the sample was approximately 20 minutes per batch processing.

FIG. 15 shows the results for a sample of negative control 1506, which was a PBS buffer solution with a volume of about 4 μl, without cells. The measurement for the negative control 1506 indicates a background signal corresponding to the buffer solution and this measurement result was removed from the measurement results of the other samples with cells so that the measurement results represent the changes induced by the cells in the respective samples, excluding the effect of the buffer solution.

FIG. 15 further shows the results for a sample with about 20% CD34 (or EPCs) cells spiked in approximately 1 μl of blood 1508, an approximate 4 μl sample with about 33%

CD34 cells spiked in a PBS buffer solution 1510 (approximately 0.99 million cells/ml of CD34 in PBS), an approximate 4 μl sample with about 80% CD34 cells spiked in a PBS buffer solution 1512 (approximately 2.4 million cells/ml of CD34 in PBS) and an approximate 4 μl sample with about 100% CD34 cells spiked in a PBS buffer solution 1514 (approximately 3 million cells/ml of CD34 in PBS). FIG. 15 shows that the signals observed correlated with the number of cells present in the sample.

Figure 16:
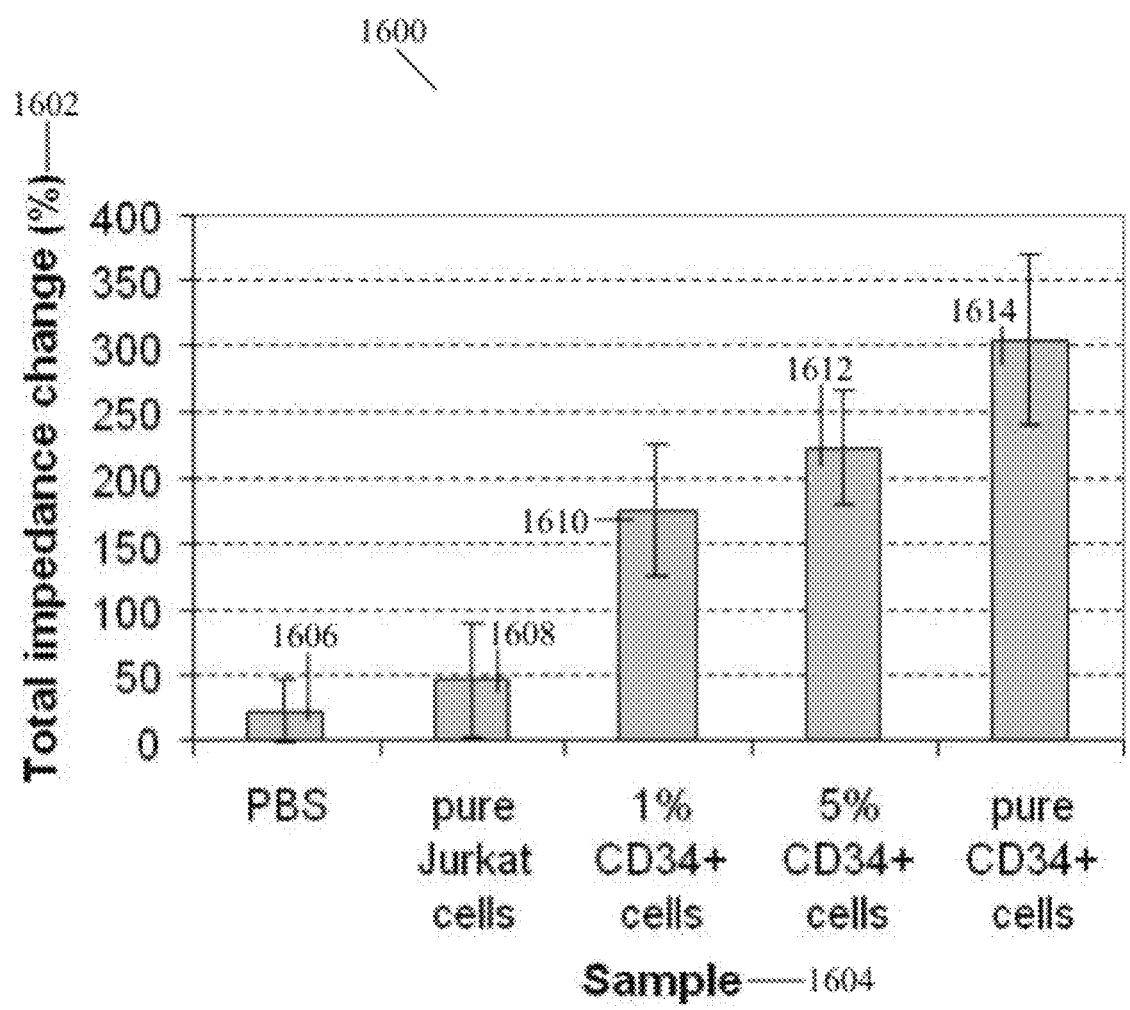
FIG. 16 shows a plot of impedance measurement for a number of samples, according to various embodiments.

FIG. 16 shows a plot 1600 of impedance measurement for a number of samples, according to various embodiments. The plot 1600 was obtained after cell purification and specific cell capture, and is shown in terms of the total impedance change (%) 1602 for 22 pairs of electrodes, against the type of sample 1604. The plot 1600 was obtained based on impedance measurement or spectroscopy carried out at the frequency of approximately 380 kHz. The detection time for the sample was approximately 20 minutes per batch processing.

FIG. 16 shows the results for a sample of approximately 4 μl PBS buffer solution without cells 1606, a pure sample of Jurkat cells 1608 (approximately 4 μl of 3 million cells/ml of Jurkat cells), a sample with about 1% CD34+ cells 1610 (approximately 4 μl of sample taken from a mixture of approximately 5 μl of 0.113 million cells/ml of CD34+ cells and approximately 10 μl of 4.44 million cells/ml of Jurkat cells), a sample with about 5% CD34+ cells 1612 (approximately 4 μl of sample taken from a mixture of approximately 5 μl of 0.563 million cells/ml of CD34+ cells and approximately 10 μl of 4.22 million cells/ml of Jurkat cells) and a pure sample of CD34+ cells 1614 (approximately 4 μl of 3 million cells/ml of CD34+ cells)

Figure 17:
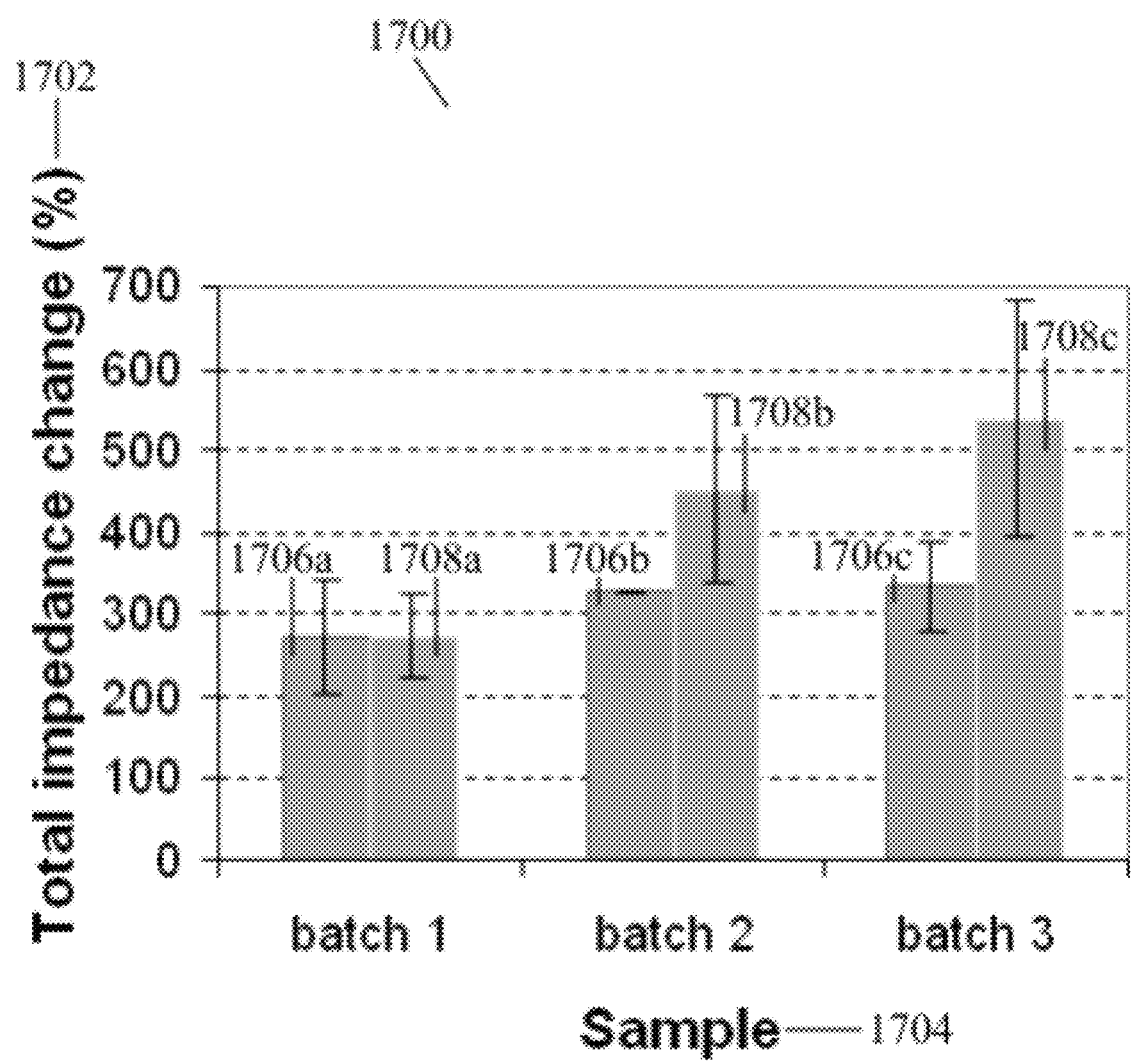
FIG. 17 shows a plot of impedance measurement for batch processing of a number of samples, according to various embodiments.

FIG. 17 shows a plot 1700 of impedance measurement for batch processing of a number of samples, according to various embodiments. The plot 1700 was obtained after cell purification and specific cell capture, and is shown in terms of the total impedance change (%) 1702 for 22 pairs of electrodes, against the type of sample 1704. The plot 1700 was obtained based on impedance measurement or spectroscopy carried out at the frequency of approximately 380 kHz.

FIG. 17 shows the results for a sample of approximately 24000 PBMC cells 1706a (Batch 1) and a sample of approximately 24000 PBMC cells spiked with about 240 CD34+ cells 1708a (Batch 1). FIG. 17 further shows that when a subsequent batch sample of approximately 24000 PBMC cells or approximately 24000 PBMC cells spiked with about 240 CD34+ cells was provided correspondingly to the Batch 1 samples, the total impedance change increased, as shown for the sample of approximately 24000 PBMC cells 1706b (Batch 2) and the sample of approximately 24000 PBMC cells spiked with about 240 CD34+ cells 1708b (Batch 2). Results for a third batch processing are shown for the sample of approximately 24000 PBMC cells 1706c (Batch 3) and the sample of approximately 24000 PBMC cells spiked with about 240 CD34+ cells 1708c (Batch 3). FIG. 17 shows that about 720 CD34+ cells spiked in the PBMC solution may be detected. The detection time for the three batches were approximately 90 minutes. For FIG. 17, each sample of approximately 24000 PBMC cells contained approximately 4 μl of 6 million cells/ml of PBMC cells while each sample of approximately 24000 PBMC cells spiked with about 240 CD34+ cells contained approximately 4 μl of sample taken from a mixture of approximately 5 μl of 0.113 million cells/ml of CD34+ cells and approximately 10 μl of 8.88 million cells/ml of PBMC cells.

Selective Cell Lysis and Detection

Magnetic beads, 1 μm in size and pre-coated with anti-CD34 antibodies, were prepared and diluted in a lysis buffer solution with suitable concentrations. The prepared lysis buffer solution with magnetic beads, in a volume of approximately 4 μl, contained a final concentration of approximately 150 mM $NH_4Cl$, 10 mM $NaHCO_3$, 0.1 mM EDTA and about 2000 magnetic beads at a ratio of 2 beads per 1 cell, suitable for 50-1000 CD34+ cells.

A blood sample was then mixed with the lysis buffer solution to form a mixture with a volume ratio of lysis buffer solution: blood of 4:1 and an approximate 10 μl mixture solution was then prepared. The mixture was incubated for about 10 minutes. In various embodiments, the mixture solution may be prepared in the range of approximately 5-100 μl.

A microfluidic system, for example the embodiment of FIG. 1A, was then used for filtration and detection. Preloading and priming of the chambers of the microfluidic system were carried out with a PBS buffer solution, provided at a flow rate of approximately 30 μl/min for about 1 minute.

The chambers were then maintained half-filled with the PBS solution. Approximately 5 μl of the prepared 10 μl mixture solution was loaded into the chambers directly or through the inlet port. Filtration and backflowing processes in accordance with various embodiments were then carried out.

A PBS solution was provided through the inlet port (ie. the first port) at a filtering flow rate of approximately 3 μl/min for about 6 minutes to remove biological entity or cells not of interest, such as RBCs. At the end of the filtration process, the chambers were maintained half-filled and left to stand for about 5 minutes. After filtration, most of the EPCs may be retained at the filter, while most of the red blood cells and other cells are removed to waste through the outlet port (ie. the second port).

In order to recover the EPCs retained at the filter and to enable the capture and detection of the EPCs, a PBS solution was provided through the outlet port in a backflowing process to push out the cells on the filter, thereby removing the cells from the filter and transferring the cells to the chambers or the detection regions of the chambers. The PBS solution was provided through the outlet port at a backflow rate of approximately 600 μl/min until the chambers were fully filled.

The filtering process was repeated by flowing in a PBS solution through the inlet port at a filtering flow rate of approximately 3 μl/min for about 2 minutes. At the end of the filtration process, the chambers were maintained half-filled.

The backflowing process was repeated by flowing in a PBS solution through the outlet port at a backflow rate of approximately 600 μl/min until the chambers were fully filled.

It should be appreciated that the filtration process may be performed for any number of times, to maximize the retention of EPCs and remove other biological entities through the filter and the backflowing process may be performed for any number of times to increase the recovery efficiency.

The sample with the EPCs was then incubated in the chambers for about 15 minutes.

The EPCs may be captured on the microelectrode array in the detection regions of the chambers by specific cell capture based on antibody-antigen recognition. In order to enhance the trapping efficiency of the EPCs on the microelectrode array, a movably arranged magnet, configured to provide or generate a magnetic field, was provided in a vicinity of the microelectrode array. The generated magnetic field may help to trap the EPCs that have been magnetically labelled on the microelectrode array.

The magnet was then removed and a washing process was performed at a washing rate of approximately 15 μl/min for about 3 minutes by flowing in a PBS solution through the outlet port into the chambers and out from the inlet port.

Subsequently, detection of the EPCs may be carried out using impedance measurement in accordance with various embodiments.

Figure 18:
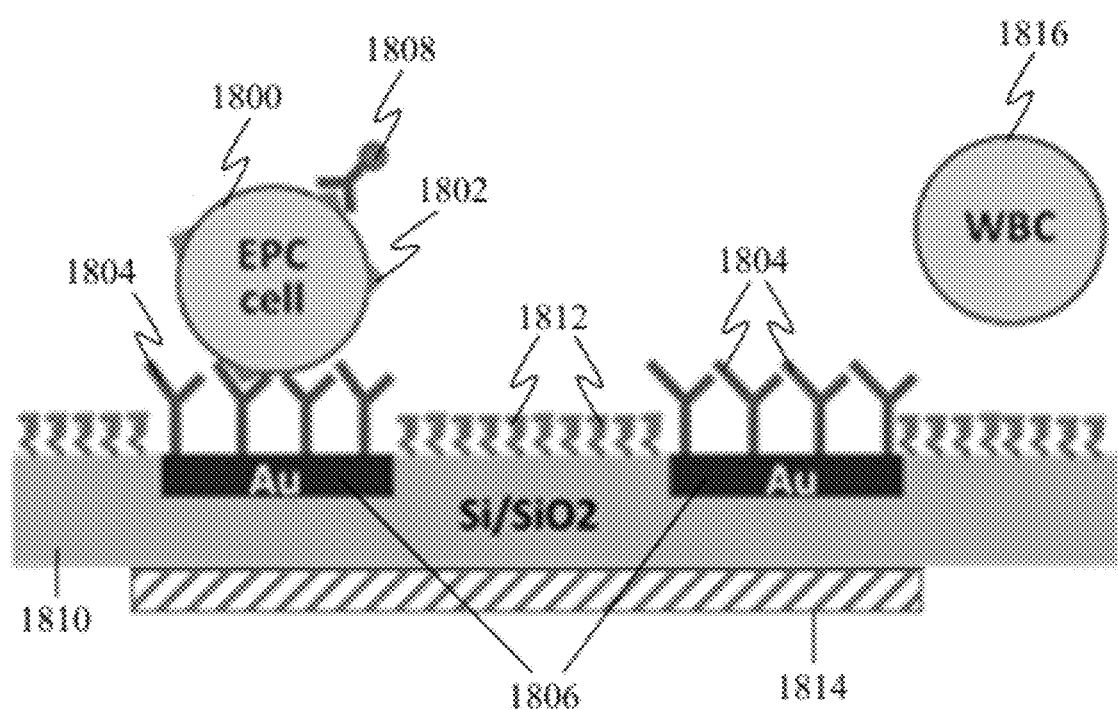
FIG. 18 shows a schematic cross sectional view illustrating the selective capture of an endothelial progenitor cell, according to various embodiments.

FIG. 18 shows a schematic cross sectional view illustrating the selective capture of an endothelial progenitor cell (EPC) 1800, according to various embodiments. The selective capture of the EPC 1800 occurs via binding of CD34 antigens, for example 1802, on the EPC 1800 with the CD34 antibodies, for example 1804, deposited or coated on the gold (Au) electrodes 1806. The EPC is further coupled with antibody-linked magnetic beads, for example 1808. As shown in FIG. 18, the gold electrodes 1806 are provided or integrated with a microchip 1810. The microchip 1810 may be a $Si/SiO_2$ microchip. The remaining portions of the microchip 1810 not covered by the electrodes 1806 may be passivated with a repellent material 1812, for example polyethylene glycol (PEG). The microfluidic system is provided with a movably arranged magnet 1814, for example a permanent magnet, in the vicinity of the electrodes 1806 for assisting in the selective magnetic trapping of the EPC 1800. As shown in FIG. 18, a white blood cell (WBC) 1816 is not captured by the CD34 antibodies 1804.

The use of immunomagnetic force may enhance the average EPC trapping efficiency by approximately 80%-100% over a non-magnetic trapping approach. Further, the trapping force may be enhanced with near-field flow and/or oscillating flow. In various embodiments, near field flow refers to the flow of the sample, such that the magnetically labelled cells may be provided as close as possible to the magnet positioned in the vicinity of the microelectrode array so that the trapping of the magnetically labelled cells may be enhanced. This may be achieved for example by lowering the height of the open chamber. In various embodiments, oscillating flow refers to the flow of the sample repeatedly, or back-and-forth through the microelectrode array or the detection region, for example by repeatedly performing the filtration and backflowing processes of various embodiments, to enhance the probability for the magnetically labelled cells to be captured on the microelectrode array.

The embodiments as described may also be used for multiple marker separation. For example, a first antibody may be coupled to the cells of interest and provided for magnetic trapping while a second antibody specific to the cells of interest may be functionalized on the surfaces of the electrodes. After removal of other cells not of interest, for example after a washing process, only specific cells coupled with both the first and second antibodies would remain on the electrodes. In various embodiments, the multiple marker separation may be performed based on the different markers, CD34 and CD133.

Figure 19:
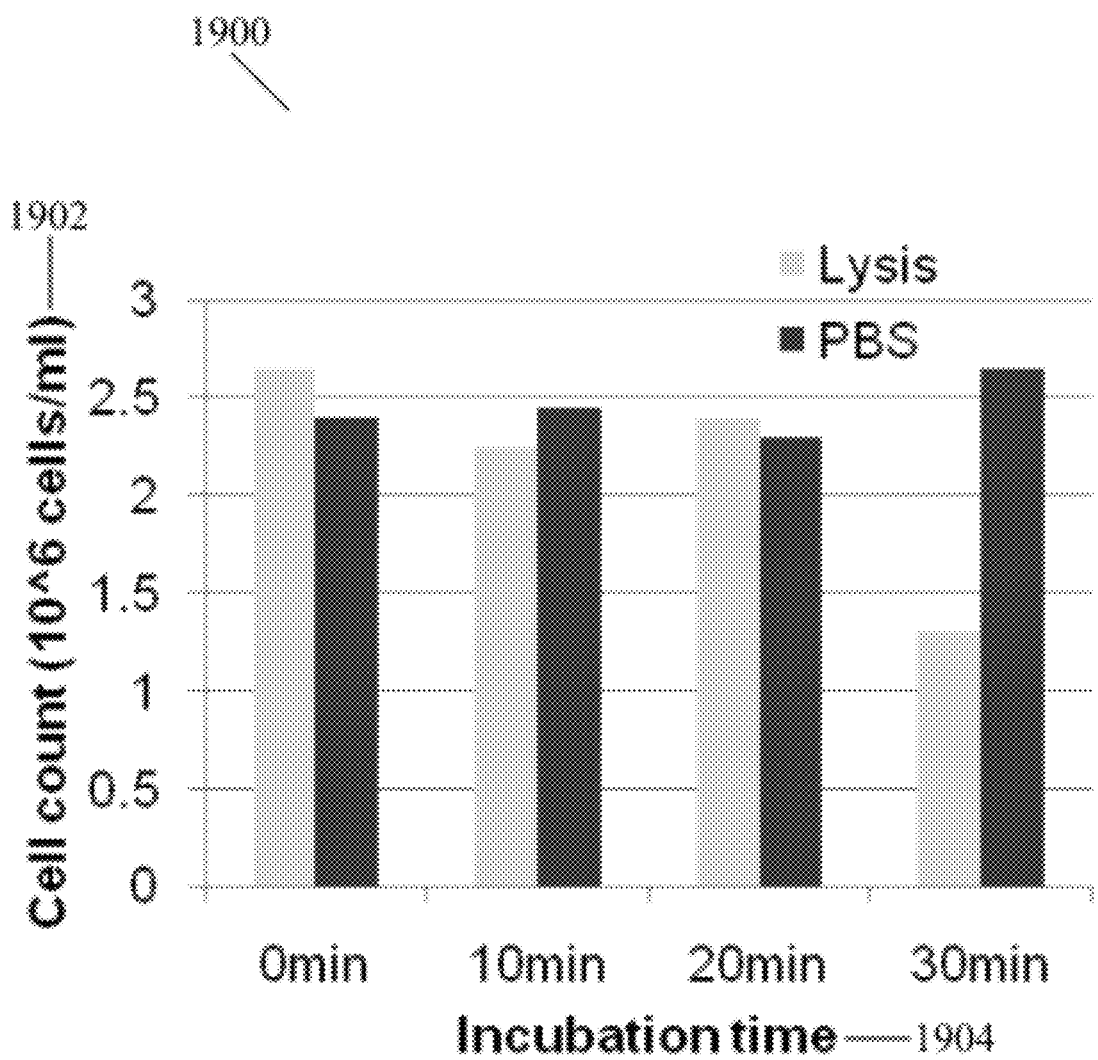
FIG. 19 shows a plot of cell count, according to various embodiments.

The effect of $NH_4Cl$ in the lysis buffer solution on the RBCs and the CD34+ cells were examined. An average of approximately 2.2 million cells/ml of CD34+ cells were mixed with the lysis buffer solution and were incubated for about 10, 20, or 30 minutes or without incubation. CD34+ cells incubated in PBS solutions were also used as the control measurements. The CD34+ cells were diluted and counted using hemocytometer after incubation. FIG. 19 shows a plot 1900 of the cell counts and is shown in terms of the cell count 1902 against incubation time 1904. FIG. 19 shows that for incubation times of 10 minutes and 20 minutes, no substantial CD34+ cell loss in the lysis buffer solution was observed. However, the viability of CD34+ cells dropped by approximately 50% when the incubation time was 30 minutes, indicating that the preferred incubation time of CD34+ cells with the lysis buffer solution is 20 minutes. In a separate measurement (result not shown), a whole blood sample with RBCs was incubated with the lysis buffer solution for about 10 minutes and the result showed that approximately 99.9% of the RBCs were lysed.

Figure 20A:
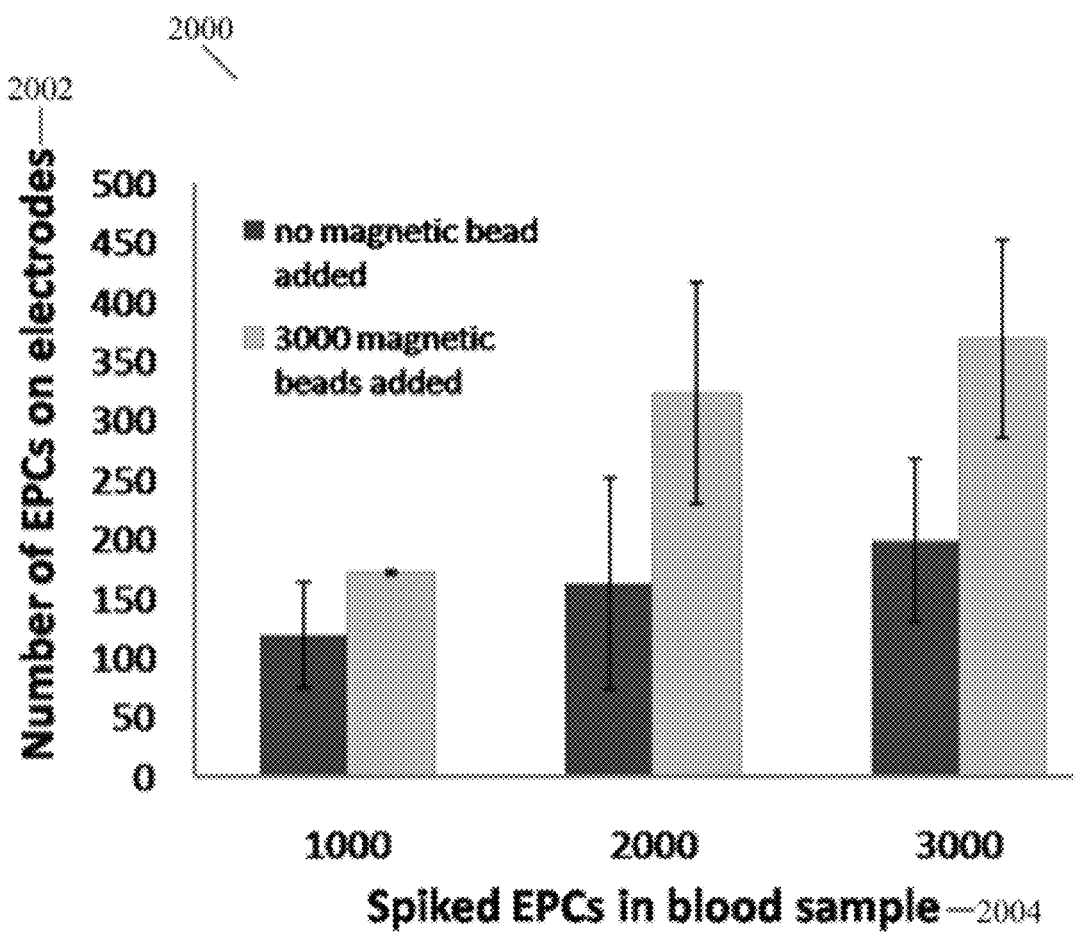
FIG. 20A shows a plot of cell count on the electrodes, according to various embodiments.
Figure 20B:
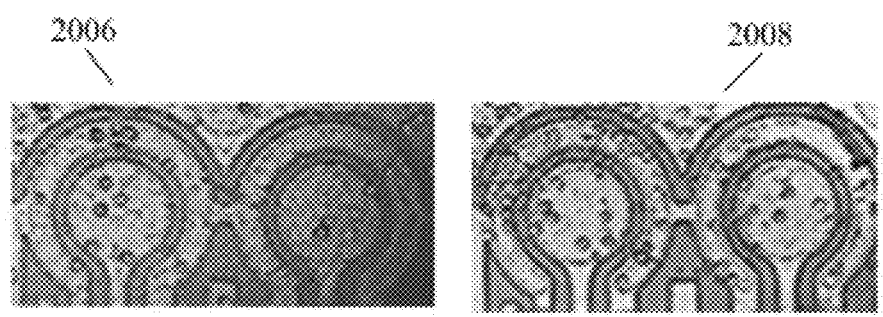
FIG. 20B shows optical microscopy images of microelectrode arrays with cells, according to various embodiments.

A comparison measurement was also conducted by applying approximately 3000 magnetic beads with a range of spiked CD34+ cells in blood (approximately 1000, 2000 and 3000 cells) to determine the improvement by immunomagnetic separation on the trapping efficiency using magnetic beads over the corresponding number of CD34+ cells without magnetic beads. FIG. 20A shows a plot 2000 of cell count and is shown in terms of the number of EPCs on electrodes 2002 against spiked EPCs in blood sample 2004. The results show that an increasing number of CD34+ cells were trapped based on the immunomagnetic method and the average trapping efficiency was improved by about 80%-100% compared to CD34+ cells without magnetic labelling. FIG. 20B (left image) shows an optical microscopy image 2006 of a microelectrode array with EPCs without magnetic labelling while FIG. 20B (right image) shows an optical microscopy image 2008 of a microelectrode array with EPCs with magnetic labelling. FIG. 20B shows that a substantially higher number of magnetically labelled EPCs were captured on the microelectrode array. Also, it can be observed that the EPCs were captured mainly on the gold microelectrode area, and not on the microchip surface, thereby suggesting minimal signal loss for subsequent impedance detection.

Figure 21:
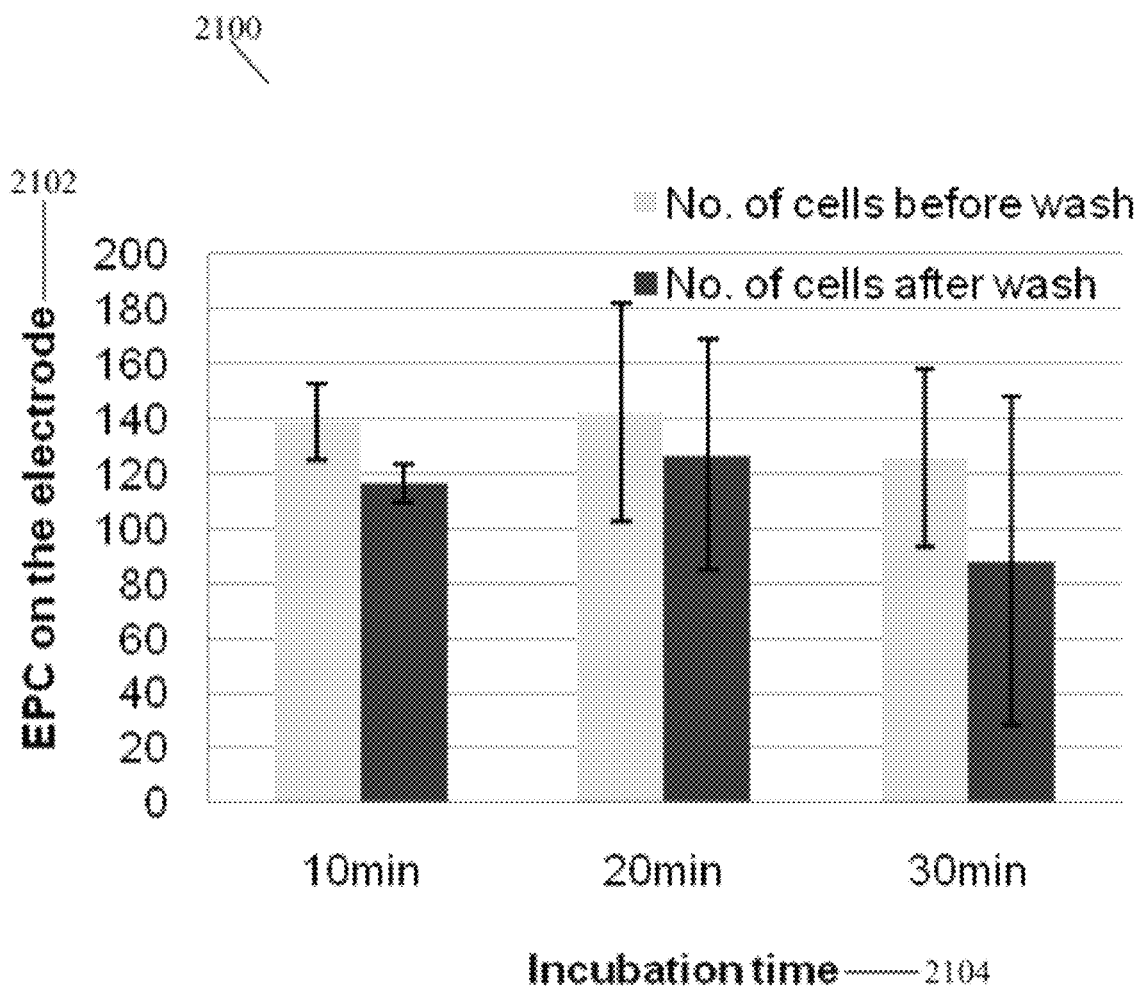
FIG. 21 shows a plot of cell count on the electrodes, according to various embodiments.

FIG. 21 shows a plot 2100 of cell count on the electrodes before and after a washing process, and is shown in terms of the EPCs on the electrode 2102 against incubation time 2104. The incubation time 2104 refers to the time provided for the attachment of the magnetic beads to the EPCs. Approximately 2000 magnetic beads were applied to the spiked CD34+ cells in blood and the blood sample was then provided to the microfluidic system of various embodiments for processing. A movably arranged magnet was used to assist in trapping the CD34+ cells on the electrode (eg. microelectrode array) and the magnet was then removed prior to washing. The results show that a number of the magnetically labelled EPCs may be washed away by a washing process. The results also indicate that there is minimal difference in the EPC retention rate on the microelectrode array (ie. number of EPCs remaining on the microelectrode array) for the incubation time of 10 minutes and 20 minutes, indicating that an incubation time of about 10 minutes is sufficient.

A comparison measurement was also conducted by applying approximately 2000 magnetic beads with a range of spiked CD34+ cells in blood (approximately 1000, 2000 and 3000 cells) to assess the retention rate of the magnetically labelled CD34+ cells over the corresponding number of CD34+ cells without magnetic beads, after removal of the magnet and after the final wash. Table 1 shows the retention rate of the EPCs on the microelectrode array for different concentrations of EPCs with magnetic beads and EPCs without magnetic beads. The results show that without the magnetic beads, around 50% of the CD34+ cells were washed away during the final washing step. However, with magnetic beads, the retention rate was improved to approximately 72.1% and 80.8%, when the cells-to-beads ratio were 1:1 and 1:2, respectively. The results indicate that the preferred number of magnetic beads is 2000 magnetic beads for a concentration of CD34+ cells in the range of 100-1000 cells (based on approximately 0.1%-1% PBMCs in 20 µl of blood).

TABLE 1

Retention rate for EPCs

| Number of EPCs | Retention rate | |
| --- | --- | --- |
| | Without beads | With beads |
| 1000 | 57.3% | 80.8% |
| 2000 | 57.6% | 72.1% |
| 3000 | 50.7% | 50.3% |

Figure 22A:
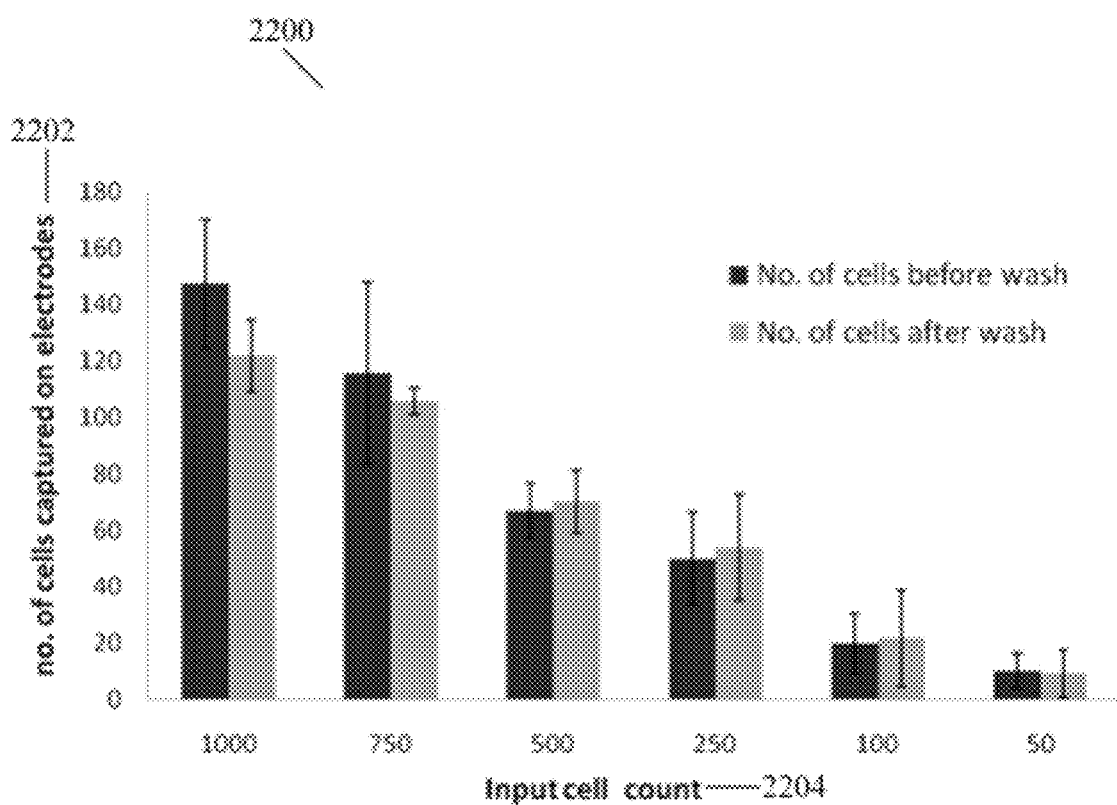
FIGS. 22A and 22B show plots of the filtration and trapping efficiency, according to various embodiments.
Figure 22B:
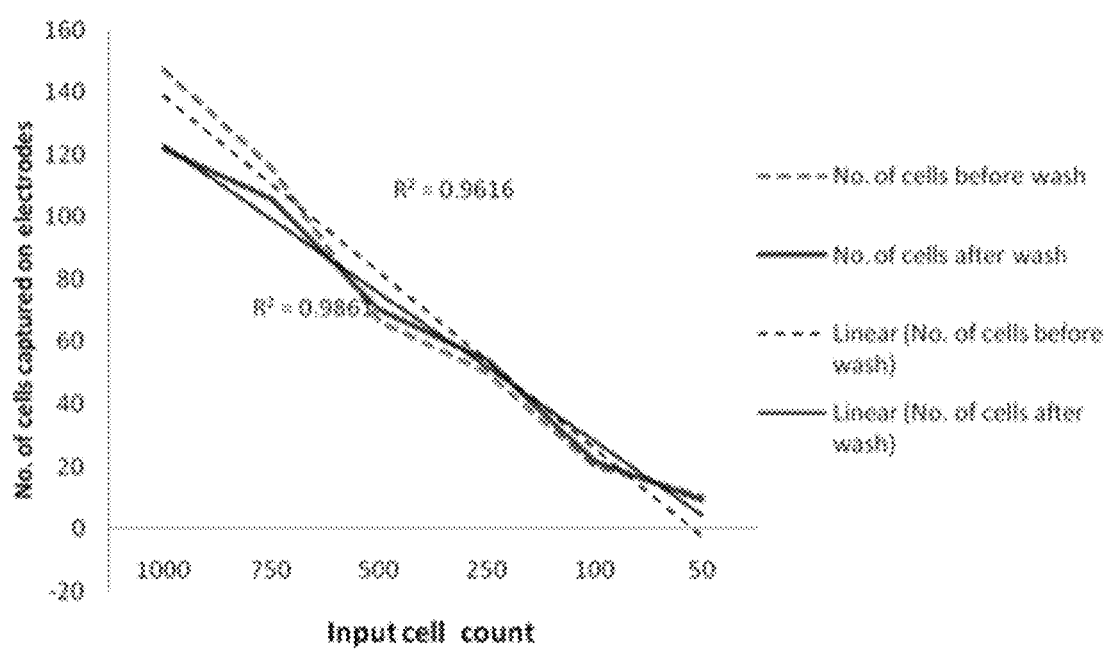

A full range characterization was carried out to determine the limit of detection of the various embodiments. A sample of approximately 50-1000 CD34+ cells spiked in blood was incubated and filtered using the processes of various embodiments and the final cell counts were examined by counting CD34+ cells on the gold electrode area using a microscope. FIG. 22A shows a plot 2200 of filtration and trapping efficiency and is shown in terms of the number of cells captured on the electrodes 2202 against the input cell count 2204 while FIG. 22B shows the linear plots and linear fits for the results of the filtration and trapping efficiency of FIG. 22A. The results shown in FIGS. 22A and 22B indicate that the detection limit may be about 100 spiked CD34+ cells (approximately 0.1% of PBMCs) with a good linear relationship of the trapping efficiency throughout the full range ($r^2=0.96$). The trapping efficiency was about 15-20% (for example about 150-200 cells per 1000 input cells may be trapped).

A comparison measurement was also conducted to assess the trapping efficiency of the magnetically labelled CD34+ cells over the corresponding number of CD34+ cells without magnetic beads, for multi-batch processing. Table 2 shows the trapping efficiency of the EPCs on the microelectrode array for different batches of EPCs with magnetic beads and EPCs without magnetic beads. For the measurements, each batch of EPCs contained approximately 1000 EPCs. The results show that, after performing a filtration process in accordance with various embodiments for a first batch of 1000 EPCs, for EPCs without magnetic beads, 62 cells out of 1000 cells were trapped on the microelectrode array, while for EPCs with magnetic beads, 153 cells were trapped. Subsequently, a second batch of approximately 1000 EPCs was added, followed by a filtration process. The results show that 68 EPCs and 214 EPCs were trapped for EPCs without magnetic beads and EPCs with magnetic beads, respectively. A third batch of approximately 1000 EPCs was then added, followed by a filtration process. The results showed that 71 EPCs and 310 EPCs were trapped for EPCs without magnetic beads and EPCs with magnetic beads, respectively. After the filtration processes involving three batches with a total of approximately 3000 EPCs, a backflow process in accordance with various embodiments was carried out to transfer the EPCs retained at the filter to the microelectrode array. The results show that 78 EPCs and 355 EPCs were trapped for EPCs without magnetic beads and EPCs with magnetic beads, respectively.

TABLE 2

Multi-batch processing

| Number of EPCs | Without beads | With beads |
| --- | --- | --- |
| 1st | 62 | 153 |
| 2nd | 68 | 214 |
| 3rd | 71 | 310 |
| Backflow | 78 | 355 |

Figure 23A:
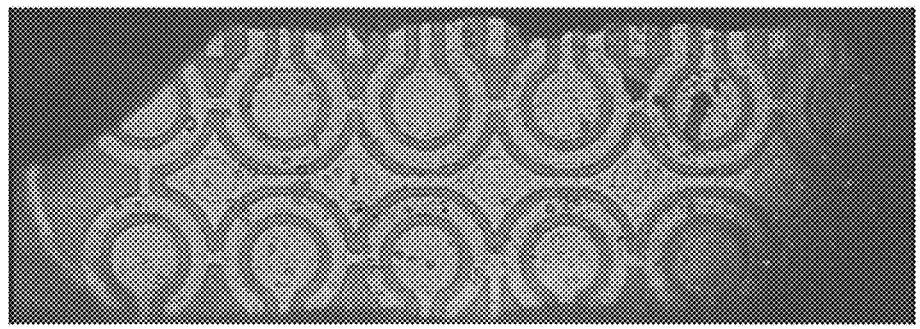
FIGS. 23A to 23D show optical microscopy images of microelectrode arrays with cells, according to various embodiments.
Figure 23B:
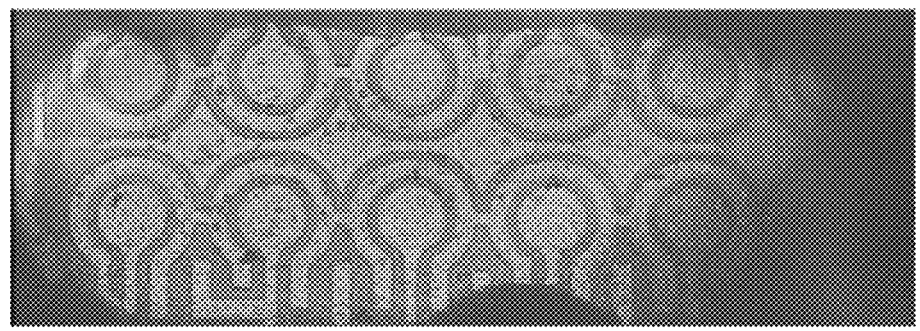
Figure 23C:
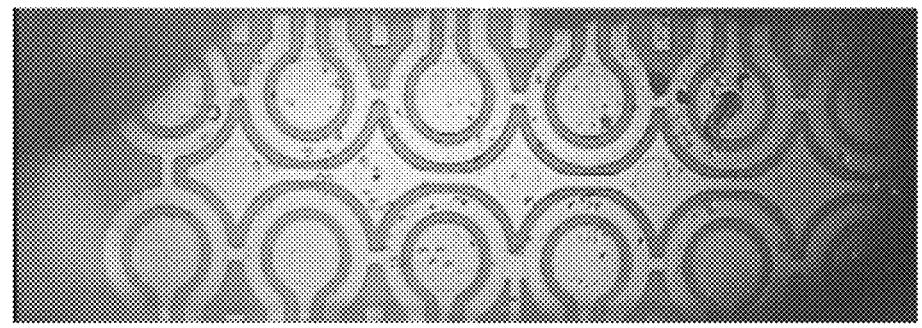
Figure 23D:
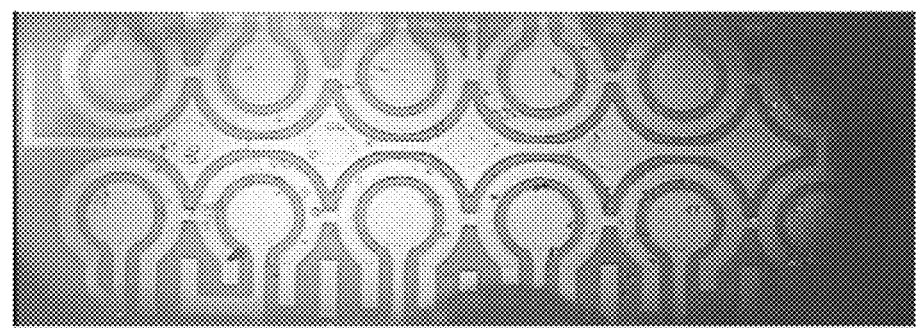

FIGS. 23A to 23D show optical microscopy images of microelectrode arrays with CD34 cells, after purification. The initial sample with the lysis buffer solution of various embodiments, contained approximately 1000 CD34 cells, 2000 magnetic beads and 3500 RBCs in about 5 μl volume. The purification or extraction of the CD34 cells involved filtration at a flow rate of about 3 μl/min for about 6 minutes and incubation for about 5 minutes. A backflow process was then performed twice, at a flow rate of about 600 μl/min that transferred the EPCs into the open chambers and then incubated for about 15 minutes. A washing process was then carried out at a flow rate of about 15 μl/min for about 3 minutes. FIGS. 23A and 23B show optical microscopy images of the microelectrode arrays with CD34 cells before the washing process while FIGS. 23C and 23D show optical microscopy images of the microelectrode arrays with CD34 cells after the washing process.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A microfluidic system for detecting a biological entity in a sample volume, the microfluidic system comprising:
   a chamber configured to receive the sample volume, wherein the chamber comprises a detection region for detecting the biological entity;
   a first port in fluid communication with the chamber; and
   a second port comprising a filter in fluid communication with the chamber; and
   wherein a fluid provided to the first port or the second port flows between the first port and the second port through the chamber such that the fluid provided to the first port passes the sample volume through the detection region and the filter to retain the biological entity at the filter, and the fluid provided to the second port transfers the biological entity retained at the filter to the detection region.

2. The microfluidic system according to claim 1, further comprising:
   at least one microchannel configured to couple the first port to the chamber; and
   at least one microchannel configured to couple the second port to the chamber.

3. The microfluidic system according to claim 1, further comprising a third or more ports in fluid communication with the chamber.

4. The microfluidic system according to claim 1, wherein the detection region is configured to detect the biological entity using a label-free detection method.

5. The microfluidic system according to claim 1, wherein the detection region comprises a microelectrode array.

6. The microfluidic system according to claim 5, further comprising capture molecules configured to attach to a surface of the microelectrode array.

7. The microfluidic system according to claim 6, wherein the fluid provided to the first port is configured to flow through the chamber and the filter such that the biological entity is retained by the filter and the fluid provided to the second port is configured to flow through the filter such that the biological entity is removed from the filter to the chamber for capture by the capture molecules attached to the surface of the microelectrode array.

8. The microfluidic system according to claim 5, wherein the microelectrode array is configured to generate a dielectrophoretic force.

9. The microfluidic system according to claim 5, further comprising a microchip being formed on or in the microelectrode array.

10. The microfluidic system according to claim 1, wherein the chamber comprises an open chamber.

11. The microfluidic system according to claim 1, wherein the filter comprises a membrane.

12. The microfluidic system according to claim 1, further comprising a movably arranged magnetic element arranged below the detection region, the magnetic element being configured to provide a magnetic field in a vicinity of the detection region.

13. The microfluidic system according to claim 1, wherein the biological entity is selected from the group consisting of a biomarker, a cell, a eukaryotic cell, a prokaryotic cell, a mammalian cell, a yeast cell, a tumour cell, a circulating tumor cell, a blood cell, a peripheral blood mononuclear cell, a cell of an immune system, a white blood cell, a T cell, a T helper cell, a lymphocyte, a CD4 lymphocyte, a progenitor cell, an endothelial progenitor cell, a fetal cell, an organelle, a virus particle, a biopolymer, a polypeptide, a nucleic acid, a lipid, an oligosaccharide, and any combination thereof.

14. A method for manufacturing a microfluidic system for detecting a biological entity in a sample volume, the method comprising:
    providing a chamber configured to receive the sample volume, wherein the chamber comprises a detection region for detecting the biological entity;
    providing a first port in fluid communication with the chamber; and
    providing a second port comprising a filter in fluid communication with the chamber; and
    wherein a fluid provided to the first port or the second port flows between the first port and the second port through the chamber such that the fluid provided to the first port passes the sample volume through the detection region and the filter to retain the biological entity at the filter, and the fluid provided to the second port transfers the biological entity retained at the filter to the detection region.

15. A method for detecting a biological entity in a sample volume using a microfluidic system for detecting a biological entity in a sample volume, the microfluidic system comprising:
    a chamber configured to receive the sample volume, wherein the chamber comprises a detection region for detecting the biological entity;
    a first port in fluid communication with the chamber; and
    a second port comprising a filter in fluid communication with the chamber; and
    wherein a fluid provided to the first port or the second port flows between the first port and the second port through the chamber;
the method comprising:
    providing the sample volume to the chamber;
    providing the fluid to the first port to pass the sample volume through the detection region and the filter to retain the biological entity at the filter;
    providing the fluid to the second port to transfer the biological entity retained at the filter to the detection region of the chamber; and
    detecting the biological entity.

16. The method according to claim 15, further comprising trapping the biological entity in a vicinity of the detection region via a movably arranged magnetic element arranged below the detection region.

17. The method according to claim 16, wherein the sample volume comprises:
    a blood sample; and
    a lysis buffer solution; and
    wherein the lysis buffer solution comprises:
        a lysing agent;
        a pH buffer; and
        an anti-coagulant.

18. The method according to claim 17, wherein the lysis buffer solution further comprises a plurality of magnetic beads for coupling to the biological entity.

19. The method according to claim 18, wherein the lysing agent comprises ammonium chloride, the pH buffer comprises sodium bicarbonate and the anti-coagulant comprises ethylenediaminetetraacetic acid.

20. The method according to claim 19, wherein a concentration of the ammonium chloride is about 10 mM to about 150 mM.

21. The method according to claim 20, wherein a volume ratio of the ammonium chloride to the blood sample is between 1:1 to 1:10.

22. The method according to claim 21, wherein a concentration of the sodium bicarbonate is between about 10 mM to about 100 mM.

23. The method according to claim 22, wherein a concentration of the ethylenediaminetetraacetic acid is between about 0.01 mM to about 1.0 mM or about 0.1 mM.

24. The method according to claim 15, wherein providing the fluid to the first port to pass the sample volume through the filter to retain the biological entity is repeated at least one time.

25. The method according to claim 15, wherein transferring the biological entity retained at the filter to the detection region of the chamber is repeated at least one time.

26. The method according to claim 15, wherein detecting the biological entity comprises:
    incubating the biological entity; and
    performing measurements for detecting the biological entity.

27. The method according to claim 15, wherein detecting the biological entity comprises a process selected from the group consisting of dielectrophoresis, capturing by capture molecules, impedance measuring, and any combination thereof.

28. The method according to claim 15, wherein the fluid comprises a buffer solution.

* * * * *

UNITED STATES PATENT AND TRADEMARK OFFICE
CERTIFICATE OF CORRECTION

| | |
|---|---|
| PATENT NO. | : 8,372,657 B2 |
| APPLICATION NO. | : 12/908561 |
| DATED | : February 12, 2013 |
| INVENTOR(S) | : Reboud et al. |

It is certified that error appears in the above-identified patent and that said Letters Patent is hereby corrected as shown below:

<u>Title page,</u>
(75) Inventors, "Shin Yun Ng" should read --Shi Yun Ng--.

Signed and Sealed this
Twenty-fifth Day of June, 2013

Teresa Stanek Rea
*Acting Director of the United States Patent and Trademark Office*